(12) United States Patent
Yamada et al.

(10) Patent No.: US 10,751,426 B2
(45) Date of Patent: Aug. 25, 2020

(54) COMPOSITION STABLY CONTAINING SINGLE-STRANDED NUCLEIC ACID MOLECULE THAT SUPPRESSES EXPRESSION OF TGF-β1 GENE

(71) Applicants: BONAC CORPORATION, Kurume-shi, Fukuoka (JP); Hirofumi Takeuchi, Gifu-shi, Gifu (JP)

(72) Inventors: Taimu Yamada, Kurume (JP); Hidekazu Toyofuku, Kurume (JP); Kohei Tahara, Gifu (JP); Risako Onodera, Gifu (JP); Hirofumi Takeuchi, Gifu (JP)

(73) Assignees: BONAC CORPORATION, Kurume (JP); Hirofumi Takeuchi, Gifu (JP)

( * ) Notice: Subject to any disclaimer, the term of this patent is extended or adjusted under 35 U.S.C. 154(b) by 104 days.

(21) Appl. No.: 15/771,305

(22) PCT Filed: Oct. 28, 2016

(86) PCT No.: PCT/JP2016/082164
§ 371 (c)(1),
(2) Date: Apr. 26, 2018

(87) PCT Pub. No.: WO2017/073767
PCT Pub. Date: May 4, 2017

(65) Prior Publication Data
US 2018/0339064 A1    Nov. 29, 2018

(30) Foreign Application Priority Data
Oct. 30, 2015    (JP) .................... 2015-215207

(51) Int. Cl.
| | | |
|---|---|---|
| *A61K 31/7105* | (2006.01) |
| *A61K 31/7125* | (2006.01) |
| *A61K 47/02* | (2006.01) |
| *A61K 47/12* | (2006.01) |
| *A61K 47/16* | (2006.01) |
| *A61K 47/18* | (2017.01) |
| *A61K 47/26* | (2006.01) |
| *A61P 11/00* | (2006.01) |
| *C07H 21/02* | (2006.01) |
| *C12N 15/09* | (2006.01) |
| *C12N 15/10* | (2006.01) |
| *C12N 15/11* | (2006.01) |
| *A61K 48/00* | (2006.01) |
| *C12N 15/113* | (2010.01) |
| *A61K 9/08* | (2006.01) |
| *C07H 21/04* | (2006.01) |

(52) U.S. Cl.
CPC .......... *A61K 48/005* (2013.01); *A61K 9/08* (2013.01); *A61K 31/7105* (2013.01); *A61K 47/02* (2013.01); *A61K 47/12* (2013.01); *A61K 47/18* (2013.01); *A61K 47/26* (2013.01); *A61K 48/00* (2013.01); *C07H 21/02* (2013.01);

*C07H 21/04* (2013.01); *C12N 15/09* (2013.01); *C12N 15/113* (2013.01)

(58) Field of Classification Search
CPC ............ A61K 31/7105; A61K 31/7125; A61K 47/02; A61K 47/12; A61K 47/16; A61K 47/18; A61K 47/26; A61P 11/00; C07H 21/02; C12N 15/09; C12N 15/10; C12N 15/11; C12N 15/111; C12N 15/113; C12N 15/1136; C12N 2310/14
See application file for complete search history.

(56) References Cited

U.S. PATENT DOCUMENTS

| | | | |
|---|---|---|---|
| 9,340,786 B2 * | 5/2016 | Khvorova ............ | C12N 15/113 |
| 2009/0143572 A1 | 6/2009 | Inomata et al. | |
| 2010/0099149 A1 * | 4/2010 | Birnboim ........... | C12N 15/1003 435/91.3 |
| 2011/0117125 A1 * | 5/2011 | Hope ................... | A61K 9/1275 424/204.1 |
| 2012/0010271 A1 | 1/2012 | Ohgi et al. | |
| 2012/0035246 A1 * | 2/2012 | Ohgi .................. | A61K 31/7105 514/44 A |
| 2012/0128756 A1 | 5/2012 | Hsu et al. | |
| 2013/0156849 A1 | 6/2013 | de Fougerolles et al. | |

(Continued)

FOREIGN PATENT DOCUMENTS

| | | |
|---|---|---|
| JP | 2007-089574 A | 4/2007 |
| JP | 2010-505396 A | 2/2010 |

(Continued)

OTHER PUBLICATIONS

Hamasaki et al, PlOS One 7(8): e42655, 2012.*

(Continued)

*Primary Examiner* — Kevin K Hill
(74) *Attorney, Agent, or Firm* — Leydig, Voit & Mayer, Ltd.

(57) ABSTRACT

The present invention provides a composition containing a single-stranded nucleic acid molecule consisting of a nucleotide sequence shown by 5'-AGCAGAGUACA-CACAGCAUAUACC-P-GGUAUAUGCUGUGUGUA-CUCUGCUUC-P-G-3' (SEQ ID NO: 1)

(in the sequence, P is a proline derivative linker represented by (I) in the DESCRIPTION) and a buffer, and having the following features:

(a) being in the form of a solution at ambient temperature; and (b) a content of the nucleic acid molecule after storage at 25° C., relative humidity 60% for 4 weeks, of not less than 80% relative to the content at the time of start of the storage.

14 Claims, 12 Drawing Sheets
Specification includes a Sequence Listing.

(56) References Cited

U.S. PATENT DOCUMENTS

| | | | |
|---|---|---|---|
| 2013/0217754 A1* | 8/2013 | Gabazza | C12N 15/113 514/44 A |
| 2013/0259942 A1 | 10/2013 | Barbe et al. | |
| 2014/0329886 A1 | 11/2014 | Ohgi et al. | |
| 2015/0051265 A1 | 2/2015 | Gao et al. | |
| 2015/0272886 A1 | 10/2015 | Chen et al. | |
| 2015/0368333 A1 | 12/2015 | Crotts et al. | |

FOREIGN PATENT DOCUMENTS

| | | |
|---|---|---|
| JP | 2010-233505 A | 10/2010 |
| JP | 2011-509258 A | 5/2011 |
| JP | 2013-537540 A | 10/2013 |
| JP | 2014-500867 A | 1/2014 |
| JP | 2015-501844 A | 1/2015 |
| JP | 2015-512372 A | 4/2015 |
| KR | 10-2015-0110659 A | 10/2015 |
| RU | 2126262 C2 | 2/1999 |
| RU | 2553375 C2 | 6/2015 |
| WO | WO 1994/006457 A1 | 5/1994 |
| WO | WO 2007/121347 A2 | 10/2007 |
| WO | WO 2011/099036 A2 | 8/2011 |
| WO | WO 2012/005368 A2 | 1/2012 |
| WO | WO 2012/017919 A1 | 2/2012 |
| WO | WO 2013/077446 A1 | 5/2013 |
| WO | WO 2013/090648 A1 | 6/2013 |
| WO | WO 2013/103146 A1 | 7/2013 |
| WO | WO 2013/133393 A1 | 9/2013 |
| WO | WO 2014/059430 A1 | 4/2014 |
| WO | WO 2015/093495 A1 | 6/2015 |
| WO | WO 2016/108264 A1 | 7/2016 |

OTHER PUBLICATIONS

Bonde et al, Biotechnol. Lett. 36: 1349-1357, 2014; available online Feb. 22, 2014.*
GenBank NM_000660.5; May 26, 2014.*
European Patent Office, Extended European Search Report in European Patent Application No. 16859995.9 (dated May 27, 2019).
Hamasaki et al., "Efficacy of a Novel Class of RNA Interference Therapeutic Agents," *PLos One*, 7(8): e42655 (2012).
Japanese Patent Office, International Search Report in International Patent Application No. PCT/JP2016/082164 (dated Dec. 6, 2016) English translation.

* cited by examiner

COMPOSITION STABLY CONTAINING SINGLE-STRANDED NUCLEIC ACID MOLECULE THAT SUPPRESSES EXPRESSION OF TGF-β1 GENE

CROSS-REFERENCE TO RELATED APPLICATIONS

This patent application is the U.S. national phase of International Patent Application No. PCT/JP2016/082164, filed Oct. 28, 2016, which claims the benefit of Japanese Patent Application No. 2015-215207, filed on Oct. 30, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 835 bytes ASCII (Text) file named "739033SequenceListing-Replacement.txt," created Mar. 12, 2020.

TECHNICAL FIELD

The present invention relates to a composition containing a single-stranded nucleic acid molecule that inhibits expression of TGF-β1 gene, which is a novel composition, particularly a pharmaceutical composition, showing improved stability of the nucleic acid molecule.

BACKGROUND ART

Pulmonary fibrosis is a disease in which fibrosis occurs in the stroma of the lung triggered by injury and collapse of pulmonary alveoli. In many cases, the cause is unknown. When the cause cannot be found, the pulmonary fibrosis is particularly termed idiopathic pulmonary fibrosis (IPF). As fibrosis progresses, the lungs harden and the oxygen exchange capacity decreases. At present, there is no definitive treatment method, and its treatment method is almost symptomatic therapy.

TGF-β is known as a cytokine that regulates cell proliferation and differentiation and is considered to also play an important role in liver or lung fibrillization. Thus, it is attracting attention as a treatment target of pulmonary fibrosis.

Nucleic acid medicine is expected as a next-generation drug discovery technology because it has both easy manufacturability of low molecular pharmaceutical products, and effectiveness and safety of antibody drugs. However, the development of the pharmaceutical products is not progressing as expected due to the barriers of instability of nucleic acid molecules in the body, side effects due to enhanced innate immune response, absence of development of efficient drug delivery system (DDS) and the like.

In the case of respiratory diseases, pulmonary fibrosis is an effective target disease of nucleic acid medicine, since topical administration of drugs to the lung is possible. To deal with the problems of nucleic acid molecule such as stability in the body and induction of innate immune response, a single-stranded nucleic acid molecule in which the terminals of a double-stranded nucleic acid of siRNA or miRNA are linked by various linkers has been developed (e.g., patent documents 1-5). Hamasaki et al. reported that symptoms were remarkably improved by intratracheal administration of a single-stranded nucleic acid molecule having the following structure carrying a TGF-β1 expression-inhibitory sequence (hereinafter to be also referred to as "PK-0051") to model mice of pulmonary fibrosis and acute lung injury (non-patent document 1).

(SEQ ID NO: 1)
5'-AGCAGAGUACACACAGCAUAUACC (SEQ ID NO: 2)
-P-GGUAUAUGCUGUGUGUACUCUGCUUC-P-G-3'

(Underline shows a TGF-β1 expression inhibitory sequence. P is a proline derivative linker represented by the following formula (I)).

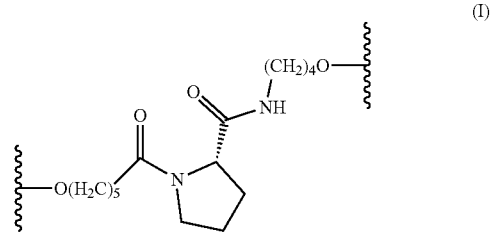

DOCUMENT LIST

Patent Documents patent document 1: WO 2012/017919
patent document 2: WO 2013/103146
patent document 3: WO 2012/005368
patent document 4: WO 2012/077446
patent document 5: WO 2013/133393

Non-Patent Document non-patent document 1: PLoS One, 2012, 7(8):e42655.

SUMMARY OF THE INVENTION

Problems to be Solved by the Invention

Generally, since nucleic acids are susceptible to decomposition in solutions and unstable, handling at ambient temperature is extremely difficult. Therefore, freeze-drying storage and a method including adding 50% ethanol to a Tris-EDTA (TE) buffer and storing same without freezing at −20° C. have generally been adopted. Under the circumstances, the development of a stable nucleic acid preparation capable of ensuring stable presence of a nucleic acid as an active ingredient at ambient temperature and excellent in handling property is desired.

Therefore, the present invention aims to provide a composition, particularly pharmaceutical composition, stably containing a single-stranded nucleic acid molecule (PK-0051), confirmed to have a treatment effect on pulmonary fibrosis or acute lung injury, as a solution at ambient temperature, and a production method thereof.

Means of Solving the Problems

The present inventors have conducted intensive studies in an attempt to solve the aforementioned problems and unexpectedly found that PK-0051 molecule can be stored stably for a long term by dissolving PK-0051 in a buffer and controlling the pH of the PK-0051 solution to fall within a particular range, which resulted in the completion of the present invention.

Therefore, the present invention is as follows.

[1] A composition comprising a single-stranded nucleic acid molecule consisting of a nucleotide sequence shown by 5'-AGCAGAGUACACACAGCAUAUACC (SEQ ID NO: 1) -P-GGUAUAUGCUGUGUGUACUCUGCUUC (SEQ ID NO: 2) -P-G-3' (in the sequence, P is a proline derivative linker represented by the following formula (I))

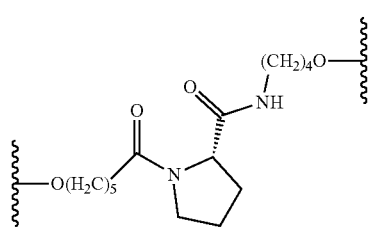

and a buffer, and having the following features:
(a) being in the form of a solution at ambient temperature; and
(b) a content of the nucleic acid molecule after storage at 25° C., relative humidity 60% for 4 weeks, of not less than 80% relative to the content at the time of start of the storage.
[2] The composition of [1], wherein the content of the nucleic acid molecule after storage at 40° C., relative humidity 75% for 4 weeks is not less than 80% relative to the content at the time of start of the storage.
[3] The composition of [1] or [2], wherein the content of the nucleic acid molecule after storage at 60° C. for 4 weeks is not less than 60% relative to the content at the time of start of the storage.
[4] The composition of [1], wherein the content of the nucleic acid molecule exposed to the total light exposure 1.2 million Lux·hr is not less than 80% relative to the content at the time of start of the storage.
[5] The composition of any of [1] to [4], wherein the buffer adjusts the pH of the composition to not less than 4.0 and not more than 9.0.
[6] The composition of any of [1] to [4], wherein the buffer adjusts the pH of the composition to not less than 4.4 and not more than 7.4.
[7] The composition of any of [1] to [4], wherein the buffer adjusts the pH of the composition to not less than 4.6 and not more than 7.0.
[8] The composition of any of [1] to [4], wherein the buffer adjusts the pH of the composition to not less than 5.5 and not more than 6.5.
[9] The composition of any of [1] to [8], wherein the buffer comprises one or more buffering agents selected from sodium hydrogen phosphate, sodium dihydrogen phosphate, disodium hydrogen phosphate, sodium chloride, arginine hydrochloride, sodium citrate, trisodium citrate dihydrate, monosodium L-glutamate, sodium acetate, sodium carbonate, sodium hydrogen carbonate, sodium lactate, monopotassium phosphate, sodium hydroxide, meglumine, glycine, citric acid, and acetic acid.
[10] The composition of any of [1] to [9], wherein the buffer comprises citric acid and/or phosphoric acid.

[11] The composition of any of [1] to [10], further comprising an isotonicity agent.
[12] The composition of [11], wherein the isotonicity agent is one or more selected from D-sorbitol, sodium chloride, glycerol, D-mannitol, potassium chloride, lactitol and sucrose.
[13] The composition of any of [1] to [12], which is for the prophylaxis or treatment of pulmonary fibrosis or acute lung injury.
[14] A method of producing the composition of any of [1] to [13], comprising dissolving the aforementioned nucleic acid molecule in a buffer adjusting a pH of the composition to not less than 4.6 and not more than 7.0, and storing the solution at ambient temperature.
[15] A method of producing the composition of any of [1] to [13], comprising dissolving the aforementioned nucleic acid molecule in a buffer adjusting a pH of the composition to not less than 5.5 and not more than 6.5, and storing the solution at ambient temperature.
[16] The method of [14] or [15], wherein the buffer comprises citric acid and/or phosphoric acid.
[17] The method of any of [14] to [16], wherein the composition is for the prophylaxis or treatment of pulmonary fibrosis or acute lung injury.
[18] A method for stabilizing a nucleic acid molecule in a composition, comprising dissolving the nucleic acid molecule in a buffer adjusting a pH of the composition to not less than 4.6 and not more than 7.0, and storing the solution at ambient temperature.
[19] A method for stabilizing a nucleic acid molecule in a composition, comprising dissolving the nucleic acid molecule in a buffer adjusting a pH of the composition to not less than 5.5 and not more than 6.5, and storing the solution at ambient temperature.
[20] The method of [18] or [19], wherein the buffer comprises citric acid and/or phosphoric acid.
[21] The method of any of [18] to [20], wherein the solution is a composition for the prophylaxis or treatment of pulmonary fibrosis or acute lung injury.

Effect of the Invention

According to the present invention, a novel and easily handleable pharmaceutical composition showing improved stability of a single-stranded nucleic acid molecule as an active ingredient and not requiring redissolving when in use can be provided.

DESCRIPTION OF EMBODIMENTS

Figure 1:
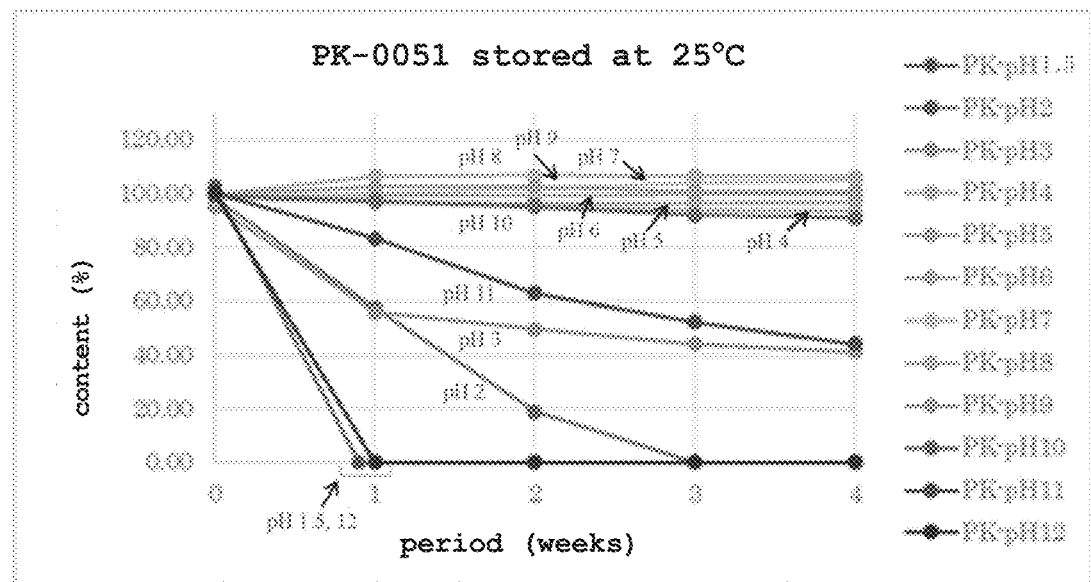
FIG. 1 shows the results of a stability test at 25° C. of PK-0051 solution prepared using a buffer at each pH.

The present invention provides a composition containing a nucleic acid molecule which is capable of stably storing single-stranded nucleic acid molecule PK-0051 containing a nucleotide sequence that inhibits expression of TGF-β1 gene in the form of a solution at ambient temperature (hereinafter to be also referred to as "the composition of the present invention"). As used herein, the "ambient temperature" means a temperature range of 15-30° C., and "stably storing" means that not less than 80% of the nucleic acid molecule at the time of start of the storage (on preparation of composition) is stored without decomposition for (1) not less than 4 weeks, preferably (2) not less than 24 weeks (about 6 months), more preferably (3) not less than 200 weeks (about 3.7 years). Such storage stability can be each confirmed or predicted from the results of the following stability test.

(1) The content of nucleic acid molecule in a composition after storage at 25° C., relative humidity 60% for 4 weeks is not less than 80% relative to the content at the time of start of the storage.

(2) The content of nucleic acid molecule in a composition after storage at 40° C., relative humidity 75% for 4 weeks is not less than 80% relative to the content at the time of start of the storage.

(3) The content of nucleic acid molecule in a composition after storage at 60° C. for 4 weeks is not less than 60%, preferably not less than 70%, more preferably not less than 80% relative to the content at the time of start of the storage. Alternatively, the content of nucleic acid molecule in a composition after storage at 105° C. for 15 min or at 121° C. for 15 min is not less than 60%, preferably not less than 70%, more preferably not less than 80% relative to the content at the time of start of the storage.

The composition of the present invention can be stably stored under high temperature conditions. Also, it can be stably stored even under freeze-thawing conditions.

In addition, "stably stored" preferably includes "stored stably to light". Being "stored stably to light" means that not less than 80% of the nucleic acid molecule at the time of start of the storage (on preparation of composition) is stored without decomposition even after exposure to the total light exposure of 1.2 million Lux·hr. Such storage stability can be confirmed or predicted from the fact that the content of nucleic acid molecule in a composition after storage under a 35 daylight fluorescent lamp (illuminance 1580 Lux) with a D65 lamp as a light source for 4 weeks is not less than 80% relative to the content at the time of start of the storage.

As used herein, the content of the nucleic acid molecule in the composition is determined by using a solution (100%) obtained by dissolving nucleic acid molecule in the same amount as a test sample in water for injection, and a solution obtained by mixing said solution and water for injection at ratios of 9:1, 8:2, 7:3 and 6:4 (90%, 80%, 70% and 60%, respectively) as calibration curve samples, applying 10 μL each of the calibration curve samples to HPLC to measure peak areas, plotting the measured values of respective calibration curve samples with the theoretical content (%) on the horizontal axis (X) and the peak area on the vertical axis (Y), obtaining a regression line (Y=aX+b) (calibration curve) by the least squares method, and applying the peak area of the test sample measured by HPLC under the same conditions to the calibration curve to give a theoretical content (%). The measurement conditions of the above-mentioned HPLC are as follows.

Reversed-Phase HPLC
measurement device: LC-10A SHIMAZU HPLC system (RP-HPLC), manufactured by Shimadzu Corporation
detector: ultraviolet absorption spectrophotometer (measurement wavelength: 254 nm) (manufactured by Shimadzu Corporation) column: X-Bridge OST C18 (2.5 μm, 4.6×50 mm) (manufactured by Japan Waters)
column temperature: 40° C.
mobile phase A: 50 mM TEAA (pH 7.0), 0.5% Acetonitrile
mobile phase B: 100% Acetonitrile
feed of mobile phase: The mixing ratio of mobile phase A and mobile phase B was changed as follows to control concentration gradient.

TABLE 1

| time (min) after injection | mobile phase A (vol %) | mobile phase B (vol %) |
|---|---|---|
| 0→12 | 100→60 | 0→40 | flow: 1.0 mL/min

Ion Exchange HPLC measurement device: LC-20A SHIMAZU HPLC system (AEX-HPLC), manufactured by Shimadzu Corporation detector: ultraviolet absorption spectrophotometer (measurement wavelength: 260 nm)

column: DNAPac PA-100 (4×250 mm)

column temperature: 80° C.

mobile phase A: 25 mM Tris-HCL (pH 8.0), 8 M urea, 10% Acetonitrile mobile phase B: mobile phase A, 700 mM sodium perchlorate monohydrate feed of mobile phase: The mixing ratio of mobile phase A and mobile phase B was changed as follows to control concentration gradient.

TABLE 2

| time (min) after injection | mobile phase A (vol %) | mobile phase B (vol %) |
|---|---|---|
| 0→20 | 90→60 | 10→40 | flow: 1.0 mL/min

1. Nucleic Acid Molecule

The nucleic acid molecule as an active ingredient to be contained in the composition of the present invention is shown by the following nucleotide sequence.

```
                                          (SEQ ID NO: 1)
5'-AGCAGAGUACACACAGCAUAUACC (SEQ ID NO: 2)
-P-GGUAUAUGCUGUGUGUACUCUGCUUC-P-G-3'
```

(in the sequence, P is a proline derivative linker represented by the following formula (I)).

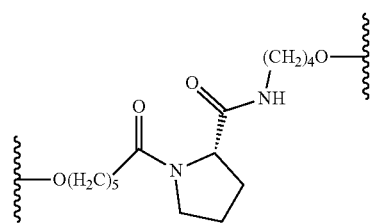

(I)

In the above-mentioned nucleotide sequence, the underlined sequence is a nucleotide sequence complementary to human TGF-β1 mRNA, and is a TGF-β1 expression inhibitory sequence that binds to the mRNA to exhibit an RNA interference action.

The nucleic acid molecule to be contained in the composition of the present invention can be produced by a method known per se. For example, it can be produced according to the method described in WO2013/133393, PLoS One, 2012, 7(8):e42655.

While the content of the nucleic acid molecule in the composition of the present invention is not particularly limited, when the composition is a pharmaceutical composition, it is generally 0.0001-60 wt %, preferably 0.001-15 wt %, further preferably 0.01-1 wt %, relative to the whole pharmaceutical composition.

2. Buffer

The composition of the present invention contains a buffer. In the present invention, the buffer refers to a solution (particularly aqueous solution) having a buffering action, and is constituted by containing a buffering agent. The buffering agent in the present invention means a stabilizer of the pH of an aqueous solution, and one generally used in the field of medicament production can be selected.

In the present invention, decomposition of the nucleic acid molecule in the composition can be prevented by using a buffer.

As a buffer to be used in the present invention, a buffer that adjusts the pH of the composition to not less than 4.0 and not more than 9.0 can be mentioned. A buffer that adjusts the pH of the composition to not less than 4.4 and not more than 7.4 is preferable, and a buffer that adjusts the pH of the composition to not less than 4.6 and not more than 7.0 is more preferable, and a buffer that adjusts the pH of the composition to not less than 5.5 and not more than 6.5 is further preferable.

As a buffering agent to be used in the present invention, specifically, one or more buffering agents selected from ascorbic acid, magnesium L-aspartate, sodium sulfite, L-arginine, L-arginine hydrochloride, benzoic acid, sodium benzoate, epsilon-aminocaproic acid, ammonium chloride, potassium chloride, sodium chloride, glucosamine chloride, hydrochloric acid triethanolamine, dilute hydrochloric acid, citric acid, anhydrous citric acid, anhydrous sodium citrate, citric acid hydrate, sodium citrate hydrate, sodium dihydrogen citrate, sodium citrate, disodium citrate, trisodium citrate, trisodium citrate dihydrate, potassium citrate, glycylglycine, glycine, glucono-σ-lactone, gluconic acid, calcium gluconate hydrate, L-glutamic acid, monosodium L-glutamate, creatinine, chlorobutanol, disodium hydrogen phosphate, sodium dihydrogen phosphate, succinic acid, disodium succinate hexahydrate, acetic acid, ammonium acetate, potassium acetate, sodium acetate hydrate, diisopropanolamine, diethanolamine, tartaric acid, sodium L-tartrate, potassium hydroxide, sodium hydroxide, taurine, sodium carbonate, sodium carbonate hydrate, sodium hydrogen carbonate, triisopropanolamine, triethanolamine, trometamol, carbon dioxide, lactic acid, calcium lactate hydrate, sodium lactate solution, L-histidine, 4-(2-hydroxyethyl), glacial acetic acid, glucose, monosodium fumarate, sodium propionate, benzalkonium chloride, aromatic hydrocarbon mixed solvent, ammonium borate, maleic acid, anhydrous sodium acetate, anhydrous sodium carbonate, disodium hydrogen phosphate anhydrate, trisodium phosphate anhydrate, sodium dihydrogen phosphate anhydrate, sodium metaphosphate, methanesulfonic acid, sulfuric acid, aluminum sulfate potassium hydrate, phosphoric acid, sodium monohydrogen phosphate heptahydrate, trisodium phosphate, dibasic sodium phosphate hydrate, disodium hydrogen phosphate hydrate, sodium dihydrogen phosphatehydrate, potassium dihydrogen phosphate, sodium dihydrogen phosphate, sodium dihydrogen phosphate monohydrate can be mentioned. Of these, a buffer containing citric acid or a salt thereof or a hydrate thereof, or phosphoric acid or a salt thereof or a hydrate thereof as a buffering agent is preferably used.

Therefore, as a buffer to be used for the composition of the present invention, a buffer containing citric acid/or phosphoric acid can be preferably mentioned.

In the present invention, the buffer preferably contains an acid exemplified as the above-mentioned buffering agent and a salt thereof, or salts of two or more kinds of acids exemplified as the above-mentioned buffering agent. More preferably, a buffer containing citric acid and a salt thereof (e.g., citric acid and sodium citrate, citric acid and trisodium citrate, and the like), a buffer containing phosphoric acid and a salt thereof (e.g., phosphoric acid and sodium dihydrogen phosphate, and the like), and a buffer containing two kinds of phosphates (e.g., disodium hydrogen phosphate and sodium dihydrogen phosphate) can be mentioned. Particularly preferred are/is a buffer containing citric acid and a salt thereof and/or a buffer containing two kinds of phosphates.

The amount of a buffer to be used for the composition of the present invention may be any as long as it can adjust to a desired pH range. For example, it can be appropriately determined to make the content of the buffering agent in the composition fall within the following range. That is, the content of the buffering agent in the composition of the present invention is generally 0.0001-40 wt %, preferably 0.0005-20 wt %, further preferably 0.001-10 wt %, relative to the whole composition.

3. Other Additives

The composition of the present invention may further contain a solvent. Examples of the solvent include pharmaceutically acceptable organic solvents (e.g., ethanol, propylene glycol, polyethylene glycol, glycerol etc.), water, water for injection, physiological saline, glucose solution and the like. One or more kinds of solvent may be used in combination.

In the present invention, a nucleic acid molecule is preferably dissolved in advance in a solvent and mixed with a buffer, since the nucleic acid molecule can be dissolved in a short time. As the solvent, water is preferable. In the present specification, unless otherwise specified, that "nucleic acid molecule is dissolved in a buffer" means not only that a nucleic acid molecule as a solid is directly dissolved in a buffer but that, as mentioned above, a nucleic acid molecule is once dissolved in a solvent such as water and the like and the obtained solution is mixed with a buffer.

In the present invention, the content of the solvent is generally not less than 0.0001 wt % and less than 100 wt %, preferably not less than 0.001 wt % and less than 100 wt %, further preferably not less than 0.005 wt % and less than 100 wt %, as the total amount relative to the whole composition.

The composition of the present invention optionally further contains an isotonicity agent. Examples of the isotonicity agent include glucose, D-sorbitol, sodium chloride, glycerol, D-mannitol, potassium chloride, lactitol, sucrose, glucose and the like. Preferable isotonicity agents are D-sorbitol, sodium chloride, glycerol, D-mannitol, potassium chloride, lactitol and sucrose, and more preferred are sodium chloride, potassium chloride and sucrose. One or more kinds of isotonicity agents may be used in combination.

When an isotonicity agent is used, the osmotic pressure ratio of the composition of the present invention (ratio of osmolarity of the composition of the present invention to osmolarity afforded by physiological saline) is preferably 0.6-1.4, more preferably 0.8-1.2, further preferably 1.0.

When the composition of the present invention is a pharmaceutical composition, the composition can be formulated as, for example, inhalant liquid, injection, liquid and the like by a known method, and administered by parenteral administration (e.g., transnasal administration, intravenous administration, instillation, intramuscular administration, subcutaneous administration etc.). In addition, it can be orally administered in a suitable dosage form (e.g., capsule etc.). A preferable administration method is inhalation of droplet particles by using a nebulizer.

When the pharmaceutical composition of the present invention is an injection, it can also be produced as a liposome preparation encapsulating a nucleic acid molecule, by dissolving the nucleic acid molecule in a buffer and contacting the obtained solution with a constituent molecule of lipid membrane. The liposome preparation can be preferably used as an injection for systemic administration, such as intravenous injection, intramuscular injection and the like.

The pharmaceutical composition of the present invention may contain a pharmaceutically acceptable additive as necessary in addition to the above-mentioned components. When the pharmaceutical composition of the present invention is an injection, examples of the additive include isotonicity agent (e.g., glucose, D-sorbitol, sodium chloride, glycerol, D-mannitol, potassium chloride, lactitol, sucrose, glucose etc.), soothing agent (e.g., benzyl alcohol etc.), preservative (e.g., methyl benzoate, paraoxybenzoates, chlorobutanol, benzyl alcohol etc.) and the like. Preferable additives are methyl benzoate, D-sorbitol, sodium chloride, glycerol, D-mannitol, potassium chloride, lactitol and sucrose. More preferable additives are sodium chloride, potassium chloride and sucrose.

When the pharmaceutical composition of the present invention is formulated as an inhalant, for example, a solution obtained by dissolving a nucleic acid molecule in a solvent such as water and the like is mixed with an aqueous solution added with a buffering agent (e.g., citric acid and a salt thereof, phosphoric acid and a salt thereof), the mixture is filtered for bacterial elimination, and the obtained drug solution is filled in a tightly-sealed container such as vial, ampoule and the like to produce an inhalant. For example, a nucleic acid molecule is mixed with an aqueous solution containing water and a buffering agent (e.g., citric acid and a salt thereof, phosphoric acid and a salt thereof), dissolved by sonication and the like, filtered for bacterial elimination, and the obtained drug solution is filled in a tightly-sealed container such as vial, ampoule and the like to produce an inhalant. While a tightly-sealed container to be used is generally a colorless and transparent borosilicate glass container, a container in which a liquid contact part on the glass inner part has quartz-like surface property can also be used.

The pharmaceutical composition of the present invention is useful for the treatment or prophylaxis of diseases involving abnormal promotion of TGF-β1 expression, particularly pulmonary fibrosis and acute lung injury, since it contains, as an active ingredient, a nucleic acid molecule capable of inhibiting expression of TGF-β1. In the present invention, "treatment" includes the meaning of improvement of disease and improvement of prognosis, and "prophylaxis" includes the meaning of prevention of onset and delay of onset.

The dose of the pharmaceutical composition of the present invention also varies depending on the drug acceptability of the subject of administration, administration route, severity of the disease and the like. For example, when it is administered as a therapeutic agent for pulmonary fibrosis as an inhalant liquid to an adult, the dose of the nucleic acid molecule as an active ingredient is about 0.001 to about 20 mg/kg body weight, preferably about 0.005 to about 5 mg/kg body weight, more preferably about 0.01 to about 1 mg/kg body weight, which can be administered in one to several portions per day.

The present invention also relates to a method for stabilizing the nucleic acid molecule in the composition, which comprises adding a buffer to the nucleic acid molecule, or a production method of a stable composition containing nucleic acid molecule. As a buffer used for this method, those similar to the aforementioned examples of the composition of the present invention can be mentioned, and a similar one is preferable.

The amount of the buffer to be added in the stabilizing/production method of the present invention may be any as long as the pH can be adjusted to a desired range. For example, the amount of the buffering agent can be appropriately determined to fall within the following range. That is, the amount of the buffering agent to be added in the stabilizing/production method of the present invention is generally 0.0001-40 wt %, preferably 0.0005-20 wt %, further preferably 0.001-10 wt %, relative to the whole composition obtained by the method.

The present invention is explained in more detail in the following by referring to Examples, which are not to be construed as limitative.

EXAMPLES

Production Example 1 (Synthesis of Single-Stranded Nucleic Acid Molecule)

A single-stranded nucleic acid molecule PK-0051 carrying an expression inhibitory sequence of TGF-β1 was synthesized by a nucleic acid synthesizer (trade name: ABI Expedite (registered trademark) 8909 Nucleic Acid Synthesis System, Applied Biosystems) based on the phosphoramidite method. For the aforementioned synthesis, RNA Phosphoramidites (2'-O-TBDMSi, trade name, Samchully Pharm. Co., Ltd.) was used as RNA amidite (hereinafter the same). The aforementioned amidite was deprotected by a conventional method. The synthesized RNA was purified by HPLC. Each RNA after purification was freeze-dried.

As the linker region, L-prolinediamideamidite was used. The underline shows an expression inhibitory sequence of human TGF-β1 gene.

```
                                           (SEQ ID NO: 1)
5'-AGCAGAGUACACACAGCAUAUACC (SEQ ID NO: 2)
-P-GGUAUAUGCUGUGUGUACUCUGCUUC-P-G-3'
```

(P is a proline derivative linker represented by the following formula (I)).

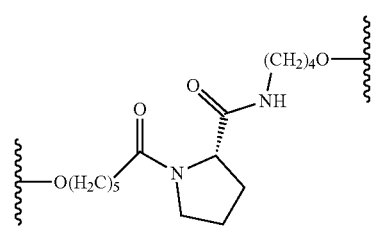

(I)

Example 1 (Evaluation of Influence of pH on Storage Temperature)

The thermal stability of PK-0051-containing composition of a prototype for inhalation of nucleic acid was evaluated.

1. Preparation of Test Composition

Test composition 1 was prepared as follows.

97.0 mL of 0.04 M hydrochloric acid, 50 mL of 0.04 M potassium chloride and 53 mL of water for injection were mixed to prepare 0.04 M hydrochloric acid-potassium chloride buffer (pH 1.0). Using the buffer, 0.1 mg/mL PK-0051 was prepared.

Test composition 2 was prepared as follows.

10 mL of 0.04 M phosphoric acid, 10 mL of 0.04 M boric acid and 10 mL of 0.04 M acetic acid were mixed, and the mixture was adjusted to pH2.0 with 2N NaOH to prepare 0.04 M Britton-Robinson buffer. Using the buffer, 0.1 mg/mL PK-0051 was prepared.

Test compositions 3-12 were prepared by a method similar to that of test composition 2 except that pH was adjusted to each pH with 2N NaOH.

test composition 1: PK-0051 (0.04 M hydrochloric acid-potassium chloride buffer (pH 1.5)), (0.1 mg/mL)
test composition 2: PK-0051 (0.04 M Britton-Robinson buffer (pH 2.0)), (0.1 mg/mL)
test composition 3: PK-0051 (0.04 M Britton-Robinson buffer (pH 3.0)), (0.1 mg/mL)
test composition 4: PK-0051 (0.04 M Britton-Robinson buffer (pH 4.0)), (0.1 mg/mL)
test composition 5: PK-0051 (0.04 M Britton-Robinson buffer (pH 5.0)), (0.1 mg/mL)
test composition 6: PK-0051 (0.04 M Britton-Robinson buffer (pH 6.0)), (0.1 mg/mL)
test composition 7: PK-0051 (0.04 M Britton-Robinson buffer (pH 7.0)), (0.1 mg/mL)
test composition 8: PK-0051 (0.04 M Britton-Robinson buffer (pH 8.0)), (0.1 mg/mL)
test composition 9: PK-0051 (0.04 M Britton-Robinson buffer (pH 9.0)), (0.1 mg/mL)
test composition 10: PK-0051 (0.04 M Britton-Robinson buffer (pH 10.0)), (0.1 mg/mL)
test composition 11: PK-0051 (0.04 M Britton-Robinson buffer (pH 11.0)), (0.1 mg/mL)
test composition 12: PK-0051 (0.04 M Britton-Robinson buffer (pH 12.0)), (0.1 mg/mL)

2. Evaluation Method

The test compositions 1-12 were respectively placed in four 5 mL glass vials, each containing 1 mL thereof, and one vial from respective compositions was stored in stability test chambers (manufactured by ESPEC CORP.) at 4° C., 25° C./60% RH, 40° C./75% RH and 60° C. The test compositions were sampled by 50 μL each and measured by HPLC every week for 4 weeks. The content of PK-0051 was calculated, and the stability was evaluated based on a decrease in the content ratio (%) relative to the content at the time of start of the storage. The calculation method of the content and measurement method are shown below.

The content of PK-0051 in the test composition was determined by using a solution (100%) obtained by dissolving PK-0051 in the same amount as the test composition in water for injection, and a solution obtained by mixing said solution and water for injection at ratios of 9:1, 8:2, 7:3 and 6:4 (90%, 80%, 70% and 60%, respectively) as calibration curve samples, applying 10 μL each of the calibration curve samples to HPLC to measure peak areas, plotting the measured values of respective calibration curve samples with the theoretical content (%) on the horizontal axis (X) and the peak area on the vertical axis (Y), obtaining a regression line (Y=aX+b) (calibration curve) by the least squares method, and applying the peak area of the test composition measured by HPLC under the same conditions to the calibration curve to give a theoretical content (%).

Measurement Method

The calibration curve samples (60%-100%) and test compositions were measured under the following measurement conditions.

detector: ultraviolet absorption spectrophotometer (measurement wavelength: 254 nm)
column: X-Bridge OST C18 (2.5 μm, 4.6×50 mm)

column temperature: 40° C.
mobile phase A: 50 mM TEAA (pH 7.0), 0.5% Acetonitrile
mobile phase B: 100% Acetonitrile
feed of mobile phase: The mixing ratio of mobile phase A and mobile phase B was changed as follows to control concentration gradient (Table 3).

TABLE 3

| time (min) after injection | mobile phase A (vol %) | mobile phase B (vol %) |
|---|---|---|
| 0→12 | 100→60 | 0→40 | flow: 1.0 mL/min
3. Results

Figure 2:
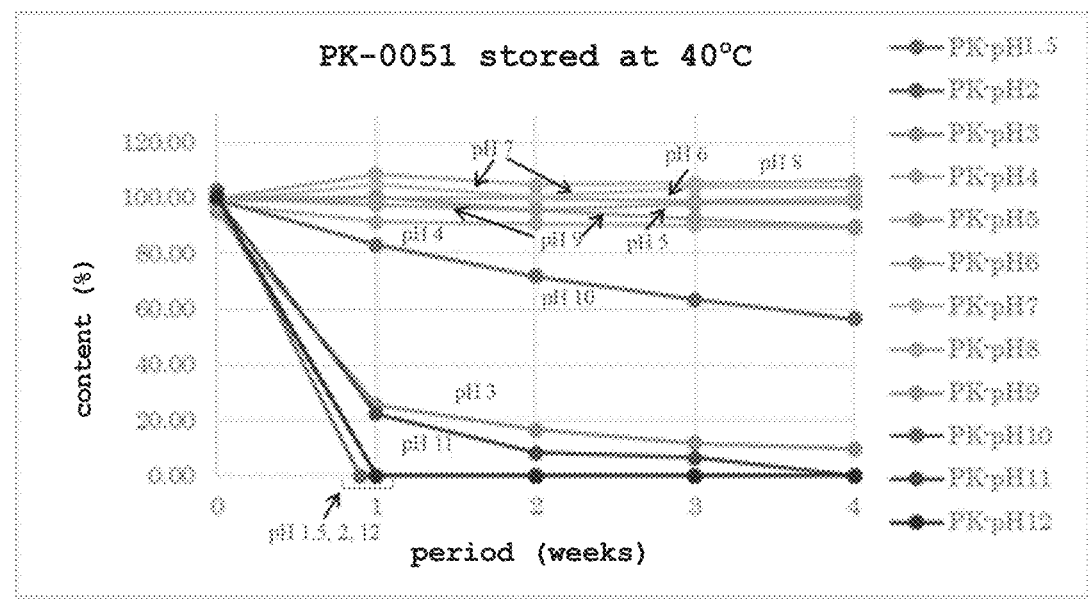
FIG. 2 shows the results of a stability test at 40° C. of PK-0051 solution prepared using a buffer at each pH.
Figure 3:
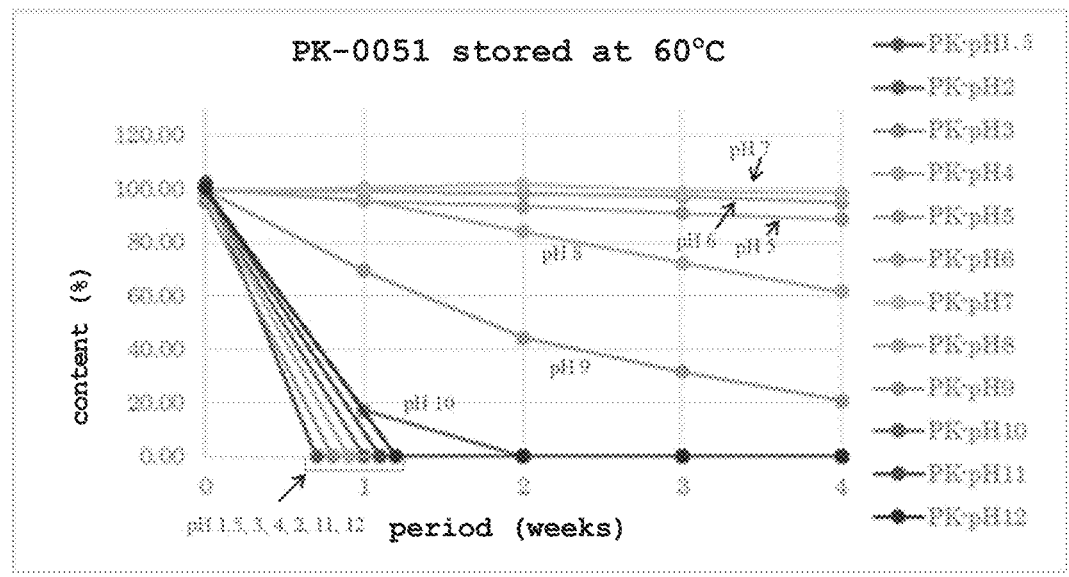
FIG. 3 shows the results of a stability test at 60° C. of PK-0051 solution prepared using a buffer at each pH.
Figure 4:
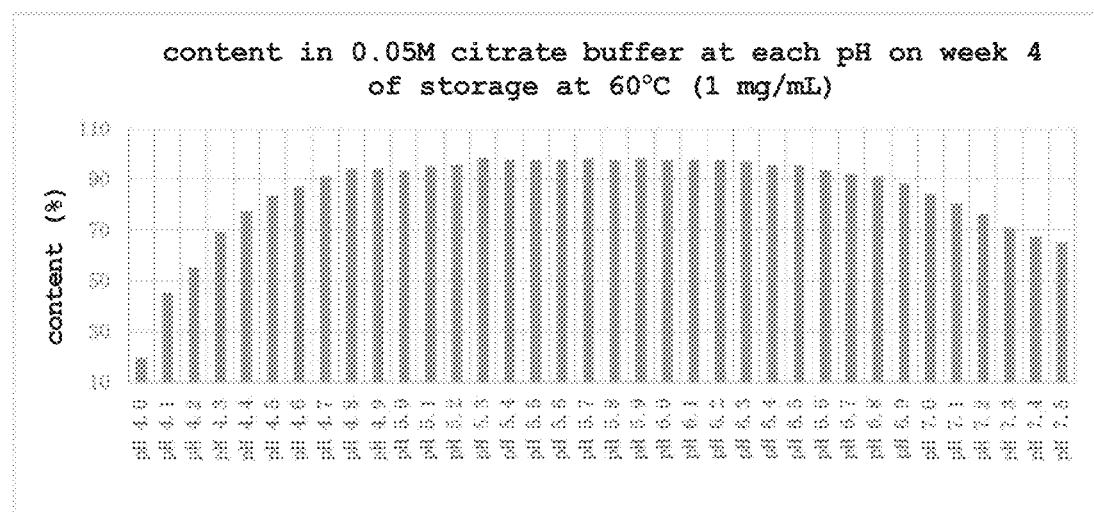
FIG. 4 shows the results of a stability test at 60° C. of PK-0051 solution prepared using a 0.05 M citrate buffer (pH 4.0-7.5).
Figure 5:
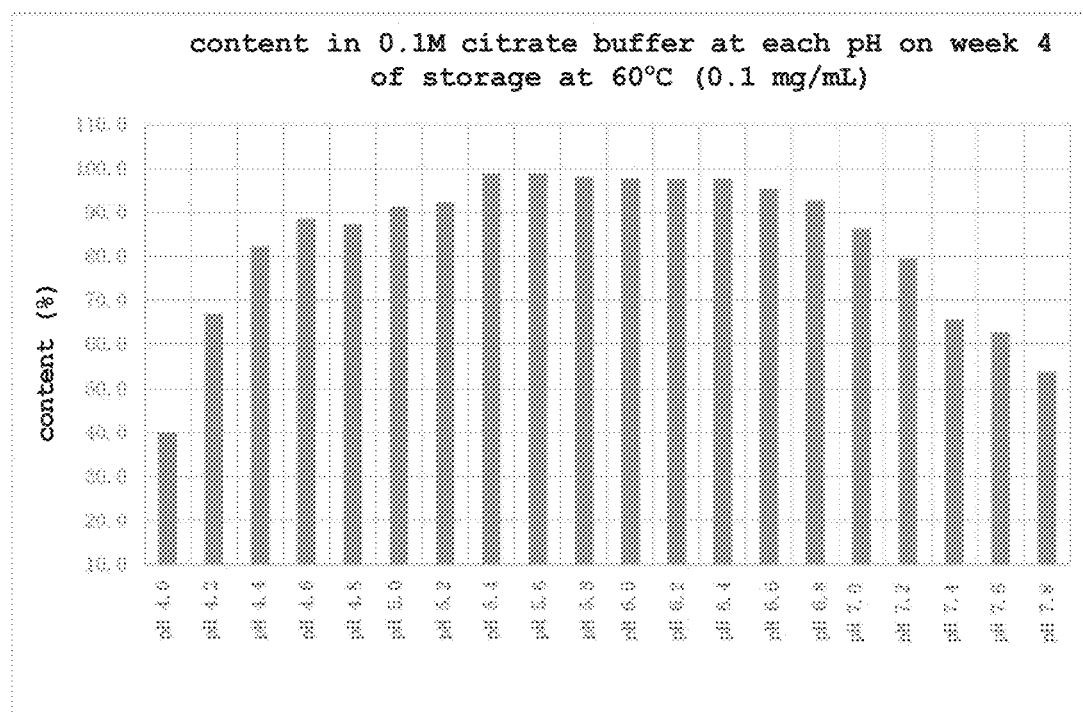
FIG. 5 shows the results of a stability test at 60° C. of PK-0051 solution prepared using a 0.1 M citrate buffer (pH 4.0-7.8).
Figure 6:
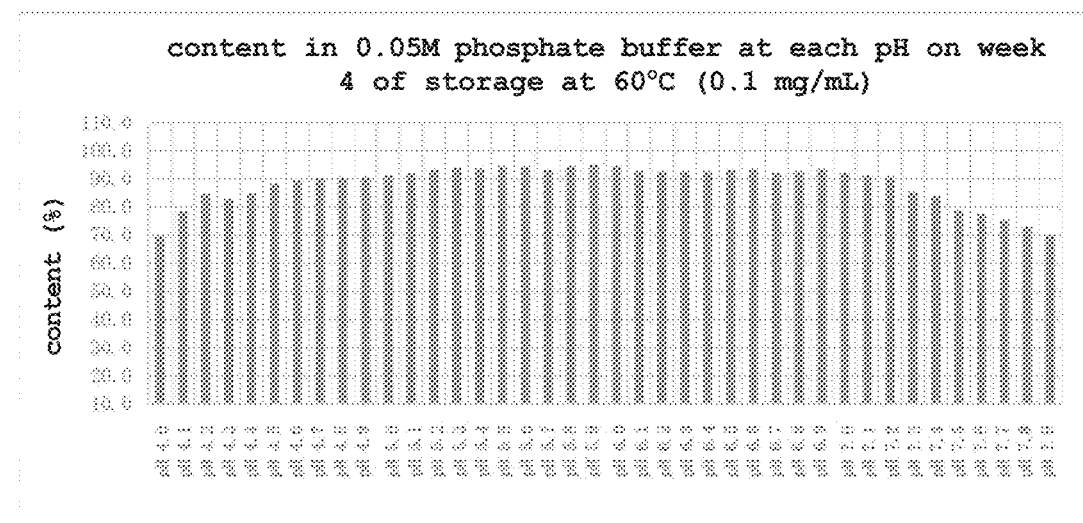
FIG. 6 shows the results of a stability test at 60° C. of PK-0051 solution prepared using a 0.05 M phosphate buffer (pH 4.0-7.9).
Figure 7:
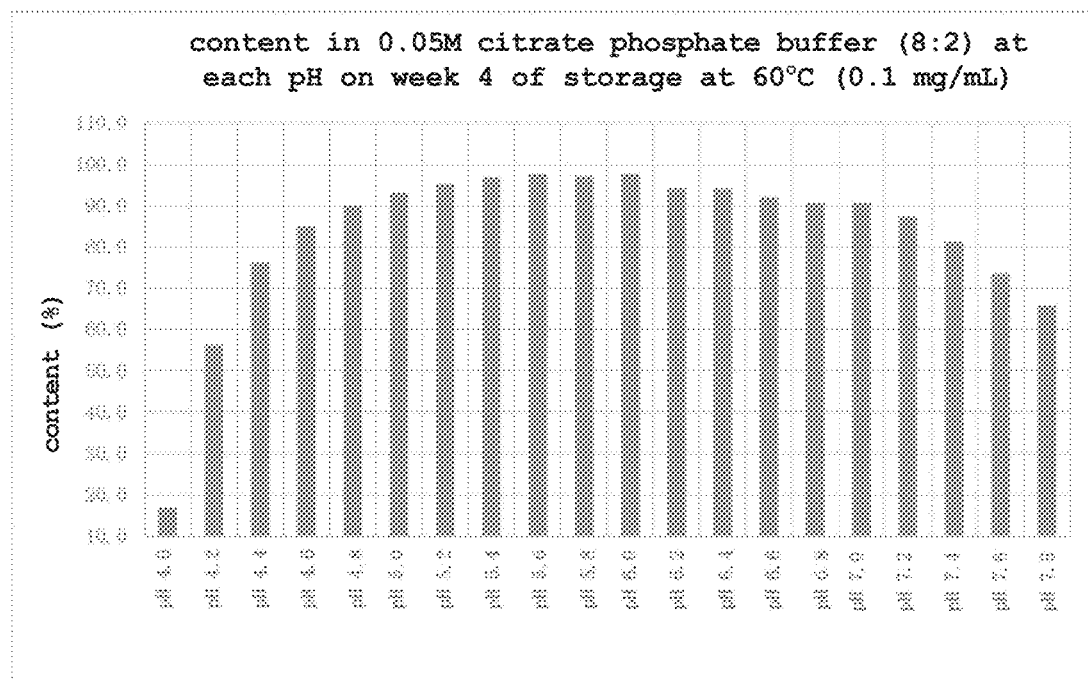
FIG. 7 shows the results of a stability test at 60° C. of PK-0051 solution prepared using 0.05 M citrate buffer:0.05 M phosphate buffer (8:2) (pH 4.0-7.8).
Figure 8:
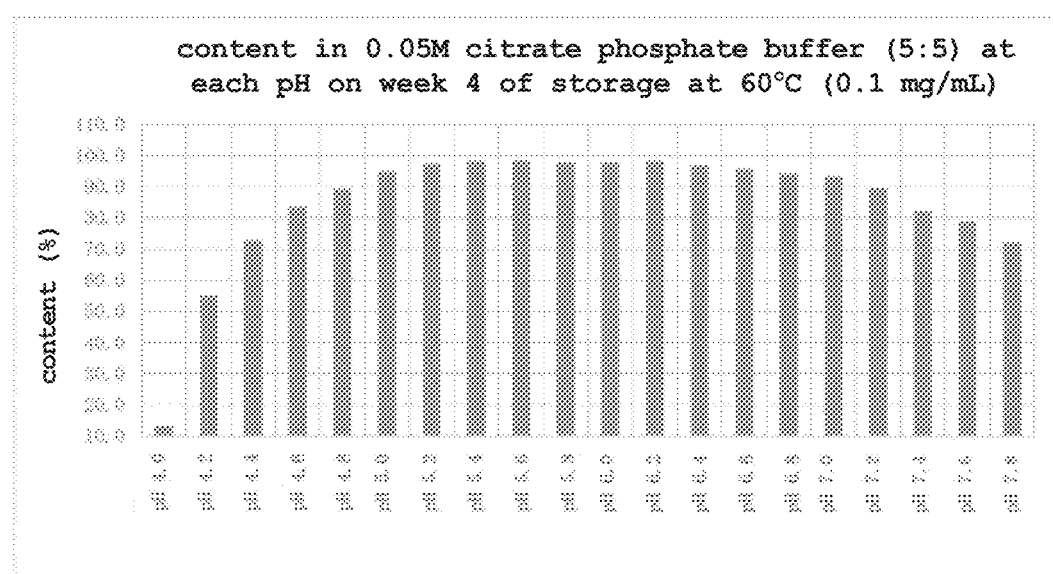
FIG. 8 shows the results of a stability test at 60° C. of PK-0051 solution prepared using 0.05 M citrate buffer:0.05 M phosphate buffer (5:5) (pH 4.0-7.8).
Figure 9:
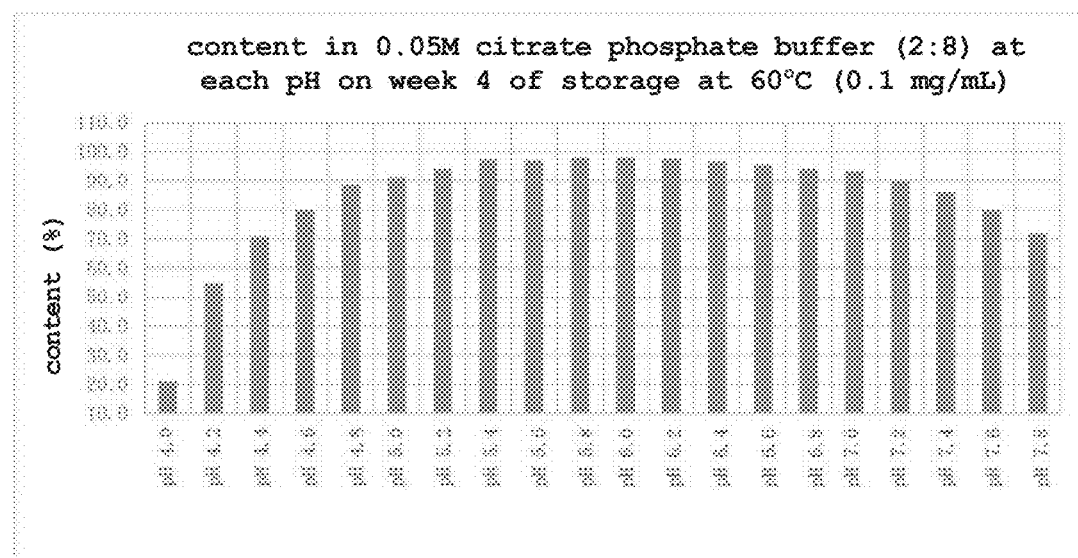
FIG. 9 shows the results of a stability test at 60° C. of PK-0051 solution prepared using 0.05 M citrate buffer:0.05 M phosphate buffer (2:8) (pH 4.0-7.8).

The results are shown in FIG. 1-FIG. 3. A clear decrease in the content was not observed within the pH range of 5-7 under the severest conditions of 60° C., 4 weeks storage.

In general, nucleic acid is easily influenced by temperature and storage thereof at ambient temperature or above for a long time is said to be impossible. The results have shown that single-stranded nucleic acid can be stored for a long term even at ambient temperature or above by controlling the pH of the solution.

Example 2 (Stability Evaluation at Different pH Using Citrate Buffer and/or Phosphate Buffer)

Various buffers of PK-0051-containing compositions of a prototype for inhalation of nucleic acid and stability at each pH were evaluated.
1. Test Composition Test compositions 13-48 were prepared as follows.

A 0.1 M aqueous solution of sodium citrate and 0.1 M aqueous solution of citric acid were mixed to prepare 0.1 M citrate buffer having each pH adjusted to pH4.0-7.5. 2.35 mg/mL PK-0051 (2.13 mL) prepared with water for injection, water for injection (0.37 mL), and 0.1 M citrate buffer (2.5 mL) at each pH were mixed to prepare 5 mL each of 1 mg/mL test compositions 13-48.

Test compositions 49-68 were prepared as follows.

A 0.1 M aqueous solution of sodium citrate and 0.1 M aqueous solution of citric acid were mixed to prepare 0.1 M citrate buffer having each pH adjusted to pH4.0-7.8. 5.8 mg/mL PK-0051 (0.086 mL) prepared with water for injection and 0.1 M citrate buffer (4.914 mL) at each pH were mixed to prepare 5 mL each of 0.1 mg/mL test compositions 49-68.

Test compositions 69-108 were prepared as follows.

A 0.1 M aqueous solution of sodium dihydrogen phosphate and 0.1 M disodium hydrogen phosphate solution were mixed to prepare 0.1 M phosphate buffer having each pH adjusted to pH4.0-7.9. 1.2 mg/mL PK-0051 (0.495 mL) prepared with water for injection, water for injection (2.505 mL), and 0.1 M phosphate buffer (3.000 mL) at each pH were mixed to prepare 6 mL each of 0.1 mg/mL test compositions 69-108.

Test compositions 109-168 were prepared as follows.

A 0.1 M aqueous solution of sodium citrate and 0.1 M aqueous solution of citric acid were mixed to prepare 0.1 M citrate buffer having each pH adjusted to pH4.0-7.8. Similarly, 0.1 M aqueous solution of sodium dihydrogen phosphate and 0.1 M disodium hydrogen phosphate solution were mixed to prepare 0.1 M citrate buffer having each pH adjusted to pH4.0-7.8. 0.1 M citrate buffer:0.1 M phosphate buffer, each having the same pH, were mixed at 8:2 (4 mL:1 mL), 5:5 (3 mL:3 mL) and 2:8 (1 mL:4 mL) to prepare 0.1 M citrate-phosphate buffer (8:2), 0.1 M citrate-phosphate buffer (5:5) and 0.1 M citrate-phosphate buffer (2:8), each having pH 4.0-7.8.

5.8 mg/mL PK-0051 (0.1 mL) prepared with water for injection, water for injection (2.9 mL) and 0.1 M citrate-phosphate buffer (8:2) (3.0 mL) at each pH were mixed to prepare 6 mL each of 0.1 mg/mL test compositions 109-128. Test compositions 129-148 were prepared by a method similar to that in test compositions 109-128 except that 0.1 M citrate-phosphate buffer (5:5) (3.0 mL) was used instead of 0.1 M citrate-phosphate buffer (8:2) (3.0 mL) at each pH. Test compositions 149-168 were prepared by a method similar to that in test compositions 109-128 except that 0.1 M citrate-phosphate buffer (2:8) (3.0 mL) was used instead of 0.1 M citrate-phosphate buffer (8:2) (3.0 mL) at each pH.
1-1. 0.05 M Citrate Buffer (pH 4.0-7.5)

test composition 13: PK-0051 (0.05 M citrate buffer (pH 4.0)), (1 mg/mL)
test composition 14: PK-0051 (0.05 M citrate buffer (pH 4.1)), (1 mg/mL)
test composition 15: PK-0051 (0.05 M citrate buffer (pH 4.2)), (1 mg/mL)
test composition 16: PK-0051 (0.05 M citrate buffer (pH 4.3)), (1 mg/mL)
test composition 17: PK-0051 (0.05 M citrate buffer (pH 4.4)), (1 mg/mL)
test composition 18: PK-0051 (0.05 M citrate buffer (pH 4.5)), (1 mg/mL)
test composition 19: PK-0051 (0.05 M citrate buffer (pH 4.6)), (1 mg/mL)
test composition 20: PK-0051 (0.05 M citrate buffer (pH 4.7)), (1 mg/mL)
test composition 21: PK-0051 (0.05 M citrate buffer (pH 4.8)), (1 mg/mL)
test composition 22: PK-0051 (0.05 M citrate buffer (pH 4.9)), (1 mg/mL)
test composition 23: PK-0051 (0.05 M citrate buffer (pH 5.0)), (1 mg/mL)
test composition 24: PK-0051 (0.05 M citrate buffer (pH 5.1)), (1 mg/mL)
test composition 25: PK-0051 (0.05 M citrate buffer (pH 5.2)), (1 mg/mL)
test composition 26: PK-0051 (0.05 M citrate buffer (pH 5.3)), (1 mg/mL)
test composition 27: PK-0051 (0.05 M citrate buffer (pH 5.4)), (1 mg/mL)
test composition 28: PK-0051 (0.05 M citrate buffer (pH 5.5)), (1 mg/mL)
test composition 29: PK-0051 (0.05 M citrate buffer (pH 5.6)), (1 mg/mL)
test composition 30: PK-0051 (0.05 M citrate buffer (pH 5.7)), (1 mg/mL)
test composition 31: PK-0051 (0.05 M citrate buffer (pH 5.8)), (1 mg/mL)
test composition 32: PK-0051 (0.05 M citrate buffer (pH 5.9)), (1 mg/mL)
test composition 33: PK-0051 (0.05 M citrate buffer (pH 6.0)), (1 mg/mL)
test composition 34: PK-0051 (0.05 M citrate buffer (pH 6.1)), (1 mg/mL)
test composition 35: PK-0051 (0.05 M citrate buffer (pH 6.2)), (1 mg/mL)
test composition 36: PK-0051 (0.05 M citrate buffer (pH 6.3)), (1 mg/mL)
test composition 37: PK-0051 (0.05 M citrate buffer (pH 6.4)), (1 mg/mL)

test composition 38: PK-0051 (0.05 M citrate buffer (pH 6.5)), (1 mg/mL)
test composition 39: PK-0051 (0.05 M citrate buffer (pH 6.6)), (1 mg/mL)
test composition 40: PK-0051 (0.05 M citrate buffer (pH 6.7)), (1 mg/mL)
test composition 41: PK-0051 (0.05 M citrate buffer (pH 6.8)), (1 mg/mL)
test composition 42: PK-0051 (0.05 M citrate buffer (pH 6.9)), (1 mg/mL)
test composition 43: PK-0051 (0.05 M citrate buffer (pH 7.0)), (1 mg/mL)
test composition 44: PK-0051 (0.05 M citrate buffer (pH 7.1)), (1 mg/mL)
test composition 45: PK-0051 (0.05 M citrate buffer (pH 7.2)), (1 mg/mL)
test composition 46: PK-0051 (0.05 M citrate buffer (pH 7.3)), (1 mg/mL)
test composition 47: PK-0051 (0.05 M citrate buffer (pH 7.4)), (1 mg/mL)
test composition 48: PK-0051 (0.05 M citrate buffer (pH 7.5)), (1 mg/mL)
1-2. 0.1 M Citrate Buffer (pH 4.0-7.8)
test composition 49: PK-0051 (0.1 M citrate buffer (pH 4.0)), (0.1 mg/mL)
test composition 50: PK-0051 (0.1 M citrate buffer (pH 4.2)), (0.1 mg/mL)
test composition 51: PK-0051 (0.1 M citrate buffer (pH 4.4)), (0.1 mg/mL) test composition 52: PK-0051 (0.1 M citrate buffer (pH 4.6)), (0.1 mg/mL)
test composition 53: PK-0051 (0.1 M citrate buffer (pH 4.8)), (0.1 mg/mL)
test composition 54: PK-0051 (0.1 M citrate buffer (pH 5.0)), (0.1 mg/mL)
test composition 55: PK-0051 (0.1 M citrate buffer (pH 5.2)), (0.1 mg/mL)
test composition 56: PK-0051 (0.1 M citrate buffer (pH 5.4)), (0.1 mg/mL)
test composition 57: PK-0051 (0.1 M citrate buffer (pH 5.6)), (0.1 mg/mL)
test composition 58: PK-0051 (0.1 M citrate buffer (pH 5.8)), (0.1 mg/mL)
test composition 59: PK-0051 (0.1 M citrate buffer (pH 6.0)), (0.1 mg/mL)
test composition 60: PK-0051 (0.1 M citrate buffer (pH 6.2)), (0.1 mg/mL)
test composition 61: PK-0051 (0.1 M citrate buffer (pH 6.4)), (0.1 mg/mL)
test composition 62: PK-0051 (0.1 M citrate buffer (pH 6.6)), (0.1 mg/mL)
test composition 63: PK-0051 (0.1 M citrate buffer (pH 6.8)), (0.1 mg/mL)
test composition 64: PK-0051 (0.1 M citrate buffer (pH 7.0)), (0.1 mg/mL)
test composition 65: PK-0051 (0.1 M citrate buffer (pH 7.2)), (0.1 mg/mL)
test composition 66: PK-0051 (0.1 M citrate buffer (pH 7.4)), (0.1 mg/mL)
test composition 67: PK-0051 (0.1 M citrate buffer (pH 7.6)), (0.1 mg/mL)
test composition 68: PK-0051 (0.1 M citrate buffer (pH 7.8)), (0.1 mg/mL)
1-3. 0.05 M Phosphate Buffer (pH 4.0-7.9)
test composition 69: PK-0051 (0.05 M phosphate buffer (pH 4.0)), (0.1 mg/mL)
test composition 70: PK-0051 (0.05 M phosphate buffer (pH 4.1)), (0.1 mg/mL)
test composition 71: PK-0051 (0.05 M phosphate buffer (pH 4.2)), (0.1 mg/mL)
test composition 72: PK-0051 (0.05 M phosphate buffer (pH 4.3)), (0.1 mg/mL)
test composition 73: PK-0051 (0.05 M phosphate buffer (pH 4.4)), (0.1 mg/mL)
test composition 74: PK-0051 (0.05 M phosphate buffer (pH 4.5)), (0.1 mg/mL)
test composition 75: PK-0051 (0.05 M phosphate buffer (pH 4.6)), (0.1 mg/mL)
test composition 76: PK-0051 (0.05 M phosphate buffer (pH 4.7)), (0.1 mg/mL)
test composition 77: PK-0051 (0.05 M phosphate buffer (pH 4.8)), (0.1 mg/mL)
test composition 78: PK-0051 (0.05 M phosphate buffer (pH 4.9)), (0.1 mg/mL)
test composition 79: PK-0051 (0.05 M phosphate buffer (pH 5.0)), (0.1 mg/mL)
test composition 80: PK-0051 (0.05 M phosphate buffer (pH 5.1)), (0.1 mg/mL)
test composition 81: PK-0051 (0.05 M phosphate buffer (pH 5.2)), (0.1 mg/mL)
test composition 82: PK-0051 (0.05 M phosphate buffer (pH 5.3)), (0.1 mg/mL)
test composition 83: PK-0051 (0.05 M phosphate buffer (pH 5.4)), (0.1 mg/mL)
test composition 84: PK-0051 (0.05 M phosphate buffer (pH 5.5)), (0.1 mg/mL)
test composition 85: PK-0051 (0.05 M phosphate buffer (pH 5.6)), (0.1 mg/mL)
test composition 86: PK-0051 (0.05 M phosphate buffer (pH 5.7)), (0.1 mg/mL)
test composition 87: PK-0051 (0.05 M phosphate buffer (pH 5.8)), (0.1 mg/mL)
test composition 88: PK-0051 (0.05 M phosphate buffer (pH 5.9)), (0.1 mg/mL)
test composition 89: PK-0051 (0.05 M phosphate buffer (pH 6.0)), (0.1 mg/mL)
test composition 90: PK-0051 (0.05 M phosphate buffer (pH 6.1)), (0.1 mg/mL)
test composition 91: PK-0051 (0.05 M phosphate buffer (pH 6.2)), (0.1 mg/mL)
test composition 92: PK-0051 (0.05 M phosphate buffer (pH 6.3)), (0.1 mg/mL)
test composition 93: PK-0051 (0.05 M phosphate buffer (pH 6.4)), (0.1 mg/mL)
test composition 94: PK-0051 (0.05 M phosphate buffer (pH 6.5)), (0.1 mg/mL)
test composition 95: PK-0051 (0.05 M phosphate buffer (pH 6.6)), (0.1 mg/mL)
test composition 96: PK-0051 (0.05 M phosphate buffer (pH 6.7)), (0.1 mg/mL)
test composition 97: PK-0051 (0.05 M phosphate buffer (pH 6.8)), (0.1 mg/mL)
test composition 98: PK-0051 (0.05 M phosphate buffer (pH 6.9)), (0.1 mg/mL)
test composition 99: PK-0051 (0.05 M phosphate buffer (pH 7.0)), (0.1 mg/mL)
test composition 100: PK-0051 (0.05 M phosphate buffer (pH 7.1)), (0.1 mg/mL)
test composition 101: PK-0051 (0.05 M phosphate buffer (pH 7.2)), (0.1 mg/mL)
test composition 102: PK-0051 (0.05 M phosphate buffer (pH 7.3)), (0.1 mg/mL)
test composition 103: PK-0051 (0.05 M phosphate buffer (pH 7.4)), (0.1 mg/mL)

test composition 104: PK-0051 (0.05 M phosphate buffer (pH 7.5)), (0.1 mg/mL)
test composition 105: PK-0051 (0.05 M phosphate buffer (pH 7.6)), (0.1 mg/mL)
test composition 106: PK-0051 (0.05 M phosphate buffer (pH 7.7)), (0.1 mg/mL)
test composition 107: PK-0051 (0.05 M phosphate buffer (pH 7.8)), (0.1 mg/mL)
test composition 108: PK-0051 (0.05 M phosphate buffer (pH 7.9)), (0.1 mg/mL)

1-4. 0.05 M Citrate Buffer: 0.05 M Phosphate Buffer (8:2) (pH 4.0-7.8)

test composition 109: PK-0051 (0.05 M citrate buffer:0.05 M phosphate buffer (8:2) (pH 4.0)), (0.1 mg/mL)
test composition 110: PK-0051 (0.05 M citrate buffer:0.05 M phosphate buffer (8:2)(pH 4.2)), (0.1 mg/mL)
test composition 111: PK-0051 (0.05 M citrate buffer:0.05 M phosphate buffer (8:2)(pH 4.4)), (0.1 mg/mL)
test composition 112: PK-0051 (0.05 M citrate buffer:0.05 M phosphate buffer (8:2)(pH 4.6)), (0.1 mg/mL)
test composition 113: PK-0051 (0.05 M citrate buffer:0.05 M phosphate buffer (8:2)(pH 4.8)), (0.1 mg/mL)
test composition 114: PK-0051 (0.05 M citrate buffer:0.05 M phosphate buffer (8:2)(pH 5.0)), (0.1 mg/mL)
test composition 115: PK-0051 (0.05 M citrate buffer:0.05 M phosphate buffer (8:2)(pH 5.2)), (0.1 mg/mL)
test composition 116: PK-0051 (0.05 M citrate buffer:0.05 M phosphate buffer (8:2)(pH 5.4)), (0.1 mg/mL)
test composition 117: PK-0051 (0.05 M citrate buffer:0.05 M phosphate buffer (8:2)(pH 5.6)), (0.1 mg/mL)
test composition 118: PK-0051 (0.05 M citrate buffer:0.05 M phosphate buffer (8:2)(pH 5.8)), (0.1 mg/mL)
test composition 119: PK-0051 (0.05 M citrate buffer:0.05 M phosphate buffer (8:2)(pH 6.0)), (0.1 mg/mL)
test composition 120: PK-0051 (0.05 M citrate buffer:0.05 M phosphate buffer (8:2)(pH 6.2)), (0.1 mg/mL)
test composition 121: PK-0051 (0.05 M citrate buffer:0.05 M phosphate buffer (8:2)(pH 6.4)), (0.1 mg/mL)
test composition 122: PK-0051 (0.05 M citrate buffer:0.05 M phosphate buffer (8:2)(pH 6.6)), (0.1 mg/mL)
test composition 123: PK-0051 (0.05 M citrate buffer:0.05 M phosphate buffer (8:2)(pH 6.8)), (0.1 mg/mL)
test composition 124: PK-0051 (0.05 M citrate buffer:0.05 M phosphate buffer (8:2)(pH 7.0)), (0.1 mg/mL)
test composition 125: PK-0051 (0.05 M citrate buffer:0.05 M phosphate buffer (8:2)(pH 7.2)), (0.1 mg/mL)
test composition 126: PK-0051 (0.05 M citrate buffer:0.05 M phosphate buffer (8:2)(pH 7.4)), (0.1 mg/mL)
test composition 127: PK-0051 (0.05 M citrate buffer:0.05 M phosphate buffer (8:2)(pH 7.6)), (0.1 mg/mL)
test composition 128: PK-0051 (0.05 M citrate buffer:0.05 M phosphate buffer (8:2)(pH 7.8)), (0.1 mg/mL)

1-5. 0.05 M Citrate Buffer: 0.05 M Phosphate Buffer (5:5) (pH 4.0-7.8)

test composition 129: PK-0051 (0.05 M citrate buffer:0.05 M phosphate buffer (5:5)(pH 4.0)), (0.1 mg/mL)
test composition 130: PK-0051 (0.05 M citrate buffer:0.05 M phosphate buffer (5:5)(pH 4.2)), (0.1 mg/mL)
test composition 131: PK-0051 (0.05 M citrate buffer:0.05 M phosphate buffer (5:5)(pH 4.4)), (0.1 mg/mL)
test composition 132: PK-0051 (0.05 M citrate buffer:0.05 M phosphate buffer (5:5)(pH 4.6)), (0.1 mg/mL)
test composition 133: PK-0051 (0.05 M citrate buffer:0.05 M phosphate buffer (5:5)(pH 4.8)), (0.1 mg/mL)
test composition 134: PK-005 (0.05 M citrate buffer:0.05 M phosphate buffer (5:5)(pH 5.0)), (0.1 mg/mL)
test composition 135: PK-0051 (0.05 M citrate buffer:0.05 M phosphate buffer (5:5)(pH 5.2)), (0.1 mg/mL)
test composition 136: PK-0051 (0.05 M citrate buffer:0.05 M phosphate buffer (5:5)(pH 5.4)), (0.1 mg/mL)
test composition 137: PK-0051 (0.05 M citrate buffer:0.05 M phosphate buffer (5:5)(pH 5.6)), (0.1 mg/mL)
test composition 138: PK-0051 (0.05 M citrate buffer:0.05 M phosphate buffer (5:5)(pH 5.8)), (0.1 mg/mL)
test composition 139: PK-005 (0.05 M citrate buffer:0.05 M phosphate buffer (5:5)(pH 6.0)), (0.1 mg/mL)
test composition 140: PK-0051 (0.05 M citrate buffer:0.05 M phosphate buffer (5:5)(pH 6.2)), (0.1 mg/mL)
test composition 141: PK-0051 (0.05 M citrate buffer:0.05 M phosphate buffer (5:5)(pH 6.4)), (0.1 mg/mL)
test composition 142: PK-0051 (0.05 M citrate buffer:0.05 M phosphate buffer (5:5)(pH 6.6)), (0.1 mg/mL)
test composition 143: PK-0051 (0.05 M citrate buffer:0.05 M phosphate buffer (5:5)(pH 6.8)), (0.1 mg/mL)
test composition 144: PK-0051 (0.05 M citrate buffer:0.05 M phosphate buffer (5:5)(pH 7.0)), (0.1 mg/mL)
test composition 145: PK-0051 (0.05 M citrate buffer:0.05 M phosphate buffer (5:5)(pH 7.2)), (0.1 mg/mL)
test composition 146: PK-0051 (0.05 M citrate buffer:0.05 M phosphate buffer (5:5)(pH 7.4)), (0.1 mg/mL)
test composition 147: PK-0051 (0.05 M citrate buffer:0.05 M phosphate buffer (5:5)(pH 7.6)), (0.1 mg/mL)
test composition 148: PK-0051 (0.05 M citrate buffer:0.05 M phosphate buffer (5:5)(pH 7.8)), (0.1 mg/mL)

1-6. 0.05 M Citrate Buffer: 0.05 M Phosphate Buffer (2:8) (pH 4.0-7.8)

test composition 149: PK-0051 (0.05 M citrate buffer:0.05 M phosphate buffer (2:8)(pH 4.0)), (0.1 mg/mL)
test composition 150: PK-0051 (0.05 M citrate buffer:0.05 M phosphate buffer (2:8)(pH 4.2)), (0.1 mg/mL)
test composition 151: PK-0051 (0.05 M citrate buffer:0.05 M phosphate buffer (2:8)(pH 4.4)), (0.1 mg/mL)
test composition 152: PK-0051 (0.05 M citrate buffer:0.05 M phosphate buffer (2:8)(pH 4.6)), (0.1 mg/mL)
test composition 153: PK-0051 (0.05 M citrate buffer:0.05 M phosphate buffer (2:8)(pH 4.8)), (0.1 mg/mL)
test composition 154: PK-0051 (0.05 M citrate buffer:0.05 M phosphate buffer (2:8)(pH 5.0)), (0.1 mg/mL)
test composition 155: PK-0051 (0.05 M citrate buffer:0.05 M phosphate buffer (2:8)(pH 5.2)), (0.1 mg/mL)
test composition 156: PK-0051 (0.05 M citrate buffer:0.05 M phosphate buffer (2:8)(pH 5.4)), (0.1 mg/mL)
test composition 157: PK-0051 (0.05 M citrate buffer:0.05 M phosphate buffer (2:8)(pH 5.6)), (0.1 mg/mL)
test composition 158: PK-0051 (0.05 M citrate buffer:0.05 M phosphate buffer (2:8)(pH 5.8)), (0.1 mg/mL)
test composition 159: PK-0051 (0.05 M citrate buffer:0.05 M phosphate buffer (2:8)(pH 6.0)), (0.1 mg/mL)
test composition 160: PK-0051 (0.05 M citrate buffer:0.05 M phosphate buffer (2:8)(pH 6.2)), (0.1 mg/mL)
test composition 161: PK-0051 (0.05 M citrate buffer:0.05 M phosphate buffer (2:8)(pH 6.4)), (0.1 mg/mL)
test composition 162: PK-0051 (0.05 M citrate buffer:0.05 M phosphate buffer (2:8)(pH 6.6)), (0.1 mg/mL)
test composition 163: PK-0051 (0.05 M citrate buffer:0.05 M phosphate buffer (2:8)(pH 6.8)), (0.1 mg/mL)
test composition 164: PK-0051 (0.05 M citrate buffer:0.05 M phosphate buffer (2:8)(pH 7.0)), (0.1 mg/mL)
test composition 165: PK-0051 (0.05 M citrate buffer:0.05 M phosphate buffer (2:8)(pH 7.2)), (0.1 mg/mL)
test composition 166: PK-0051 (0.05 M citrate buffer:0.05 M phosphate buffer (2:8)(pH 7.4)), (0.1 mg/mL)

test composition 167: PK-0051 (0.05 M citrate buffer:0.05 M phosphate buffer (2:8)(pH 7.6)), (0.1 mg/mL)
test composition 168: PK-0051 (0.05 M citrate buffer:0.05 M phosphate buffer (2:8)(pH 7.8)), (0.1 mg/mL)

2. Evaluation Method

The test compositions 13-168 were respectively placed in five 5 mL glass vials, each containing 1 mL thereof, and stored in a stability test chamber (manufactured by ESPEC CORP.) at 60° C. The test compositions were measured by HPLC on week 4. The content of PK-0051 was calculated, and the stability was evaluated based on a decrease in the content ratio (%) relative to the content at the time of start of the storage. The measurement method and the calculation method of the content were similar to those in Example 1.

3. Results

The results are shown in FIG. 4-FIG. 9. Regardless of the buffer used, the content was not less than 80% at around pH4.6-around pH 7.4 after 4 week storage at 60° C.

Example 3 (Evaluation of Stability in Citrate Buffer and Concentration Thereof)

The thermal stability of PK-0051-containing composition of a prototype for inhalation of nucleic acid was evaluated.

1. Test Composition

Test composition 169 was prepared as follows.

A 0.1 M aqueous solution of sodium citrate and 0.1 M aqueous solution of citric acid were mixed to prepare 0.1 M citrate buffer at pH6.8. 20 mg/mL PK-0051 (0.1 mL) prepared with water for injection, water for injection (9.9 mL), and 0.1 M citrate buffer (10 mL) at pH6.8 were mixed to prepare 20 mL of 0.1 mg/mL test composition 169.

Test composition 170 was prepared as follows.

A 0.1 M aqueous solution of sodium citrate and 0.1 M aqueous solution of citric acid were mixed to prepare 0.1 M citrate buffer at pH6.8. This was diluted 10-fold to give 0.01 M citrate buffer at pH6.8. 14.2 mg/mL PK-0051 (0.0704 mL) prepared with water for injection, water for injection (4.9296 mL), and 0.01 M citrate buffer (5 mL) at pH6.8 were mixed to prepare 10 mL of 0.1 mg/mL test composition 170.
test composition 169: PK-0051 (0.05 M citrate buffer (pH 6.8)), (0.1 mg/mL)
test composition 170: PK-0051 (0.005 M citrate buffer (pH 6.8)), (0.1 mg/mL)

2. Evaluation Method

The test compositions 169 and 170 were respectively placed in nine 5 mL glass vials, each containing 1 mL thereof, and four vials from respective compositions were stored in stability test chambers at 40° C./75% RH and 60° C. and one vial from respective compositions was stored at 4° C. The test compositions were measured by HPLC every week for 4 weeks. The content of PK-0051 was calculated, and the stability was evaluated based on a decrease in the content ratio (%) relative to the content at the time of start of the storage. The measurement method and the calculation method of the content were similar to those in Example 1.

3. Results

Figure 10:
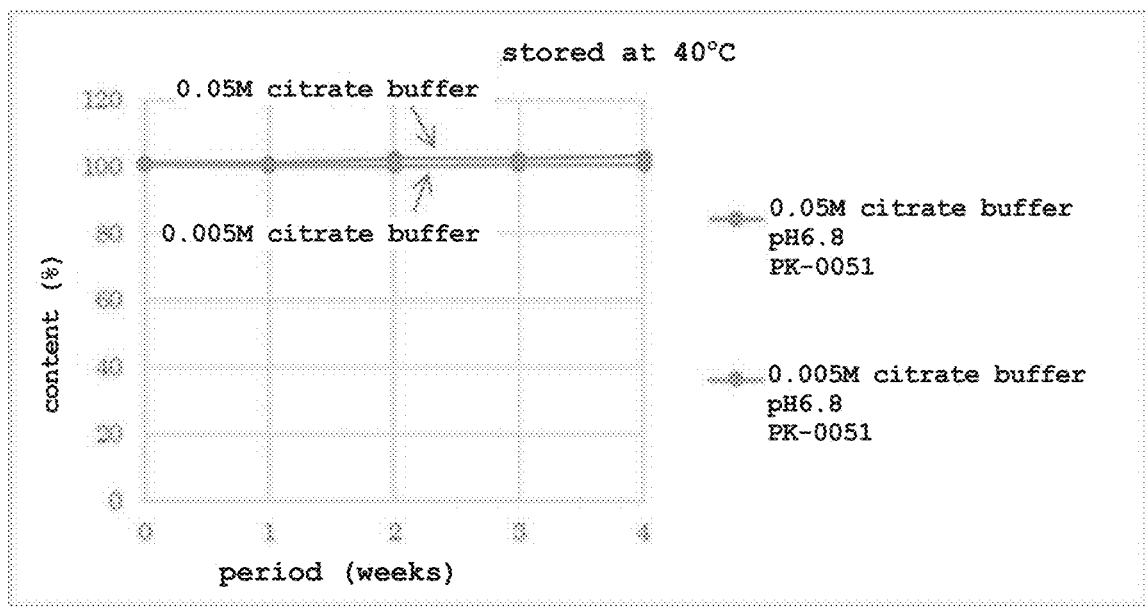
FIG. 10 shows the results of a stability test at 40° C. of PK-0051 solution prepared using a citrate buffer at each concentration.
Figure 11:
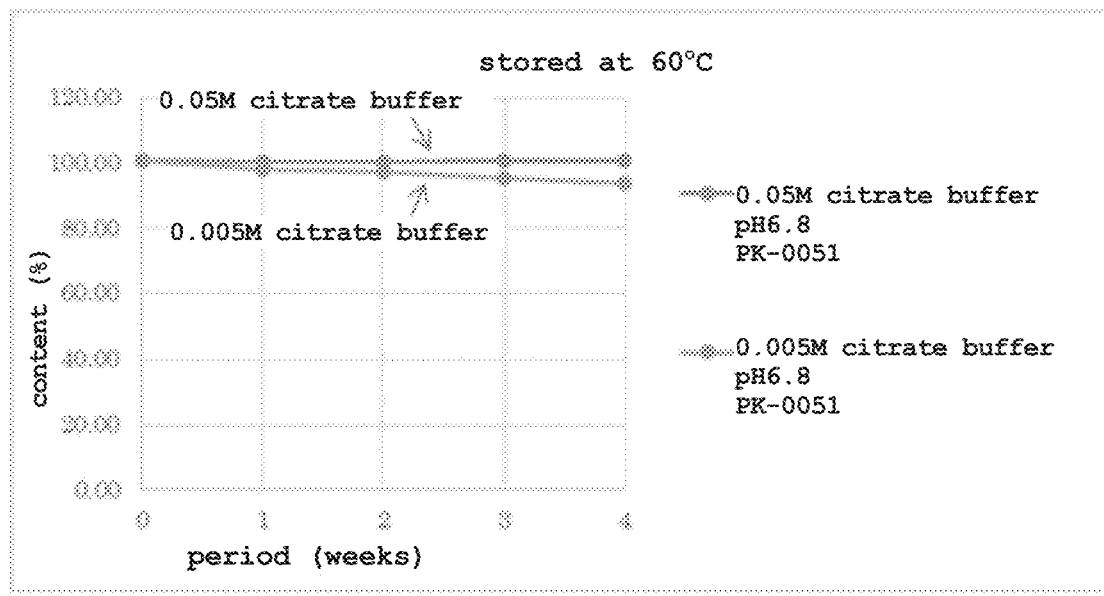
FIG. 11 shows the results of a stability test at 60° C. of PK-0051 solution prepared using a citrate buffer at each concentration.

The results are shown in FIG. 10 and FIG. 11. The results reveal that a clear content change was absent at citrate buffer concentrations of 0.005 M and 0.05 M even at 60° C., 4 weeks. Therefrom it is suggested that the effect of the stability of nucleic acid can be maintained by controlling the concentration of the citrate buffer even when the concentration of the single-stranded nucleic acid increases.

Example 4 (Stability Evaluation of PK-0051-Containing Composition (pH 6.5))

10 mg/mL and 1 mg/mL PK-0051-containing compositions (pH 6.5) were prepared and the stability was evaluated.

1. Test Composition

A 10 mg/mL PK-0051-containing composition (pH 6.5) was prepared as follows.

Citric acid hydrate (21.0 g) was dissolved in water for injection (1 L) to give 0.1 M citric acid solution. Similarly, trisodium citrate dihydrate (29.4 g) was dissolved in water for injection (1 L) to give 0.1 M sodium citrate solution. The 0.1 M citric acid solution was added to the 0.1 M sodium citrate solution to adjust the pH to 6.5 to give 0.1 M citrate buffer (pH 6.5). PK-0051 (10 g) synthesized in Production Example 1 was dissolved in water for injection (500 mL). Thereto was added 0.1 M citrate buffer (pH 6.5) (500 mL) and the mixture was stirred. The composition was passed through a 0.22 μm polyvinylidene fluoride (PVDF) filter to give 10 mg/mL PK-0051-containing composition (pH 6.5).

The 1 mg/mL PK-0051-containing composition (pH 6.5) was prepared by a method similar to the above-mentioned method except that PK-0051 was changed to 1.0 g.

Using 10 mg/mL and 1 mg/mL PK-0051-containing compositions (pH 6.5) as test compositions 171 and 172, the stability was evaluated.
test composition 171: PK-0051 (0.05 M citrate buffer (pH 6.5)), (1 mg/mL)
test composition 172: PK-0051 (0.05 M citrate buffer (pH 6.5)), (10 mg/mL)

2. Evaluation Method

The test compositions 171 and 172 were respectively placed in nine 5 mL glass vials, each containing 1 mL thereof, and four vials from respective compositions were stored in stability test chambers at 25° C./60% RH, 40° C./75% RH and 60° C. and one vial from respective compositions was stored at 4° C. The test compositions were measured by HPLC every week for 4 weeks. The content of PK-0051 was calculated, and the stability was evaluated based on a decrease in the content ratio (%) relative to the content at the time of start of the storage. The measurement method was the same as in Example 1.

The content of PK-0051 in the test composition was determined by using a solution (100%) obtained by dissolving PK-0051 in water for injection to prepare at 1 mg/mL, and a solution obtained by mixing said solution and water for injection at ratios of 9:1, 8:2, 7:3 and 6:4 (90%, 80%, 70% and 60%, respectively) as calibration curve samples, applying 10 μL each of the calibration curve samples to HPLC to measure peak areas, plotting the measured values of respective calibration curve samples with the theoretical content (%) on the horizontal axis (X) and the peak area on the vertical axis (Y), obtaining a regression line (Y=aX+b) (calibration curve) by the least squares method, and applying the peak area of the test composition measured by HPLC under the same conditions to the calibration curve to give a theoretical content (%). The content of PK-0051 in the test composition 172 was determined by a method similar to the above-mentioned method except that 1 μL was used for HPLC.

3. Results

Figure 12:
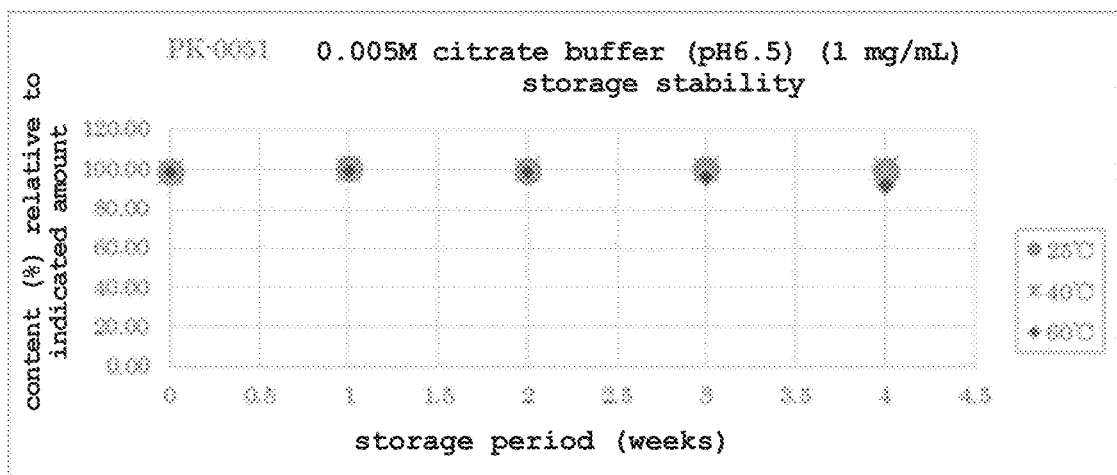
FIG. 12 shows the results of a stability test of 1 mg/mL PK-0051 solution (pH 6.5).
Figure 13:
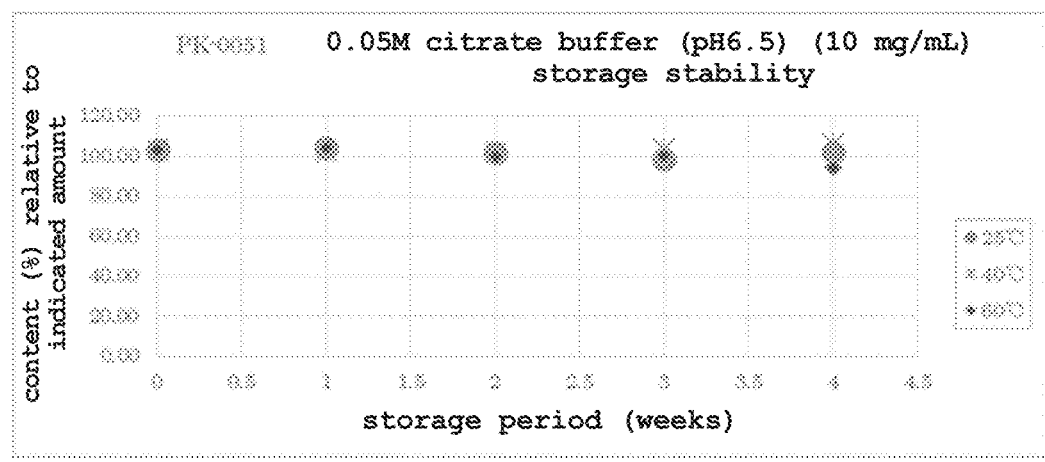
FIG. 13 shows the results of a stability test of 10 mg/mL PK-0051 solution (pH 6.5).

The results are shown in FIG. 12 and FIG. 13. The results reveal that a clear content change was absent even at 60° C., 4 weeks. Therefrom it is shown that 1 mg/mL and 10 mg/mL PK-0051-containing compositions (pH 6.5) have high stability.

Example 5 (Stability Evaluation of PK-0051-Containing Composition (pH 6.0))

A 1 mg/mL PK-0051-containing composition (pH 6.0) was prepared, and the stability was evaluated.

1. Test Composition

Citric acid hydrate (21.014 g) was dissolved in water for injection (1 L) to give 0.1 M citric acid solution. Similarly, trisodium citrate dihydrate (29.41 g) was dissolved in water for injection (1 L) to give 0.1 M sodium citrate solution. The 0.1 M citric acid solution was added to the 0.1 M sodium citrate solution to adjust the pH to 6.0 to give 0.1 M citrate buffer (pH 6.0). PK-0051 (347 mg) synthesized in Production Example 1 was dissolved in water for injection (5 mL). To this solution (0.144 mL) were added water for injection (4.856 mL) and 0.1 M citrate buffer (pH 6.0) (5 mL) and the mixture was stirred. It was passed through a 0.22 μm polyvinylidene difluoride (PVDF) filter to give 1 mg/mL PK-0051-containing composition (pH 6.0).

Using 1 mg/mL PK-0051-containing composition (pH 6.0) as test composition 173, the stability was evaluated.
test composition 173: PK-0051 (0.05 M citrate buffer (pH 6.0)), (1 mg/mL)

2. Evaluation Method

The test composition 173 was placed in five 5 mL glass vials, each containing 1 mL thereof, and one vial was stored at 4° C. and four vials were stored in a stability test chamber at 60° C. The test composition was measured by HPLC every week for 4 weeks. The content of PK-0051 was calculated, and the stability was evaluated based on a decrease in the content ratio (%) relative to the content at the time of start of the storage. The measurement method and the calculation method of the content were similar to those in Example 1.

3. Results

Figure 14:
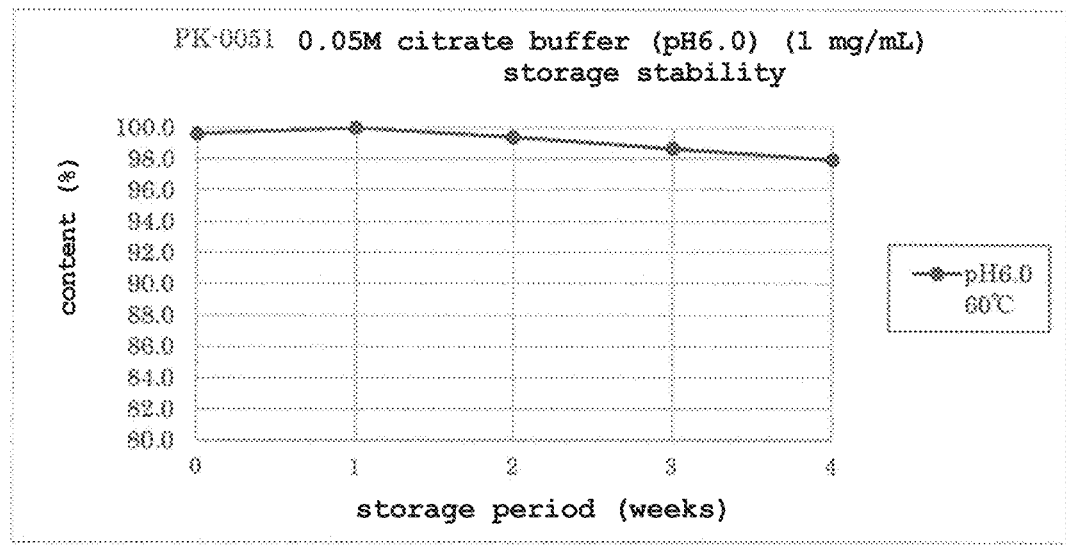
FIG. 14 shows the results of a stability test of 1 mg/mL PK-0051 solution (pH 6.0).

The results are shown in FIG. 14. The results reveal that a clear content change was absent even at 60° C., 4 weeks. Therefrom it is shown that 1 mg/mL PK-0051-containing composition (pH 6.0) have high stability.

Example 6 (Pulmonary Fibrosis Inhibitory Effect in Pulmonary Fibrosis Spontaneous Model Mouse)

Using pulmonary fibrosis spontaneous model mouse (human TGF-β1 transgenic mouse described in Am. J. Respir. Cell Mol. Biol., 2012, 46(3), 397-406 and PLoS One, 2012, 7(8):e42655, hereinafter to be referred to as TG mouse), a pulmonary fibrosis inhibitory effect of the composition of the present invention was confirmed. The aforementioned effect was confirmed using a hydroxy proline amount in the lung tissue as an index and according to the method described in PLoS One, 2012 (mentioned above).

1. Test Composition

The 10 mg/mL PK-0051-containing composition (pH 6.5) prepared in Example 4 was diluted with 0.05 M citrate buffer (pH 6.5) and used as a test composition. The dilution was performed based on the body weight of TG mouse on the day of administration of the test composition.

2. Grouping and Administration of Test Composition

Using Micro CT apparatus (R_mCT2, manufactured by Rigaku Corporation), fibrosis in the lung of TG mouse was evaluated, and the mice were grouped such that the level of pulmonary fibrosis and the body weight at the time of grouping were equivalent among respective groups.

Respective administration groups are shown in the following. In each administration group, 11 male mice were used. Under isoflurane anesthesia, the test composition was administered 4 times in total into the trachea of the TG mice by using Micro Sprayer (MSA-250-M: manufactured by PENNCENTURY).

Administration Group 1

A 0.05 M citrate buffer (pH 6.5) was administered to TG mouse once/week.

Administration Group 2

The test composition was administered to TG mouse at 5 mg/kg body weight once/two weeks.

Administration Group 3

The test composition was administered to TG mouse at 5 mg/kg body weight once/week.

3. Sampling of Lung Tissue

Pentobarbital was intraperitoneally administered to TG mice (1.22 mg/150 μL/mouse-1.62 mg/200 μL/mouse) for anesthesia, blood samples were collected and bilateral lungs were isolated and frozen for homogenate samples.

4. Quantification of hTGF-β1 in Lung Tissue

Bilateral lungs were homogenated by Beads Cell Disrupter (MS-100, manufactured by TOMY SEIKO CO., LTD.), and a part of the supernatant was recovered by centrifugation. The level of hTGF-β1 in the supernatant was determined using Human TGF-β1ELISA Set (manufactured by BD).

5. Quantification of Hydroxy Proline in Lung Tissue

Bilateral lungs after homogenization were dried by incubation at 110° C. overnight, and pulverized again using Beads Cell Disrupter. To the pulverized bilateral lungs was added 6N HCl (1 mL) and the mixture was incubated in a draft chamber at 110° C. overnight. Thereafter, the mixture was incubated in a draft chamber at 110° C. overnight. Thereto was added 2 mL of PBS and the mixture was incubated at 60° C. for 1 hr and passed through a filter to give a sample for measuring the hydroxy proline amount. The hydroxy proline amount was determined by the method of PLoS One. 2012; 7(8):e42655.

6. Results

Figure 15:
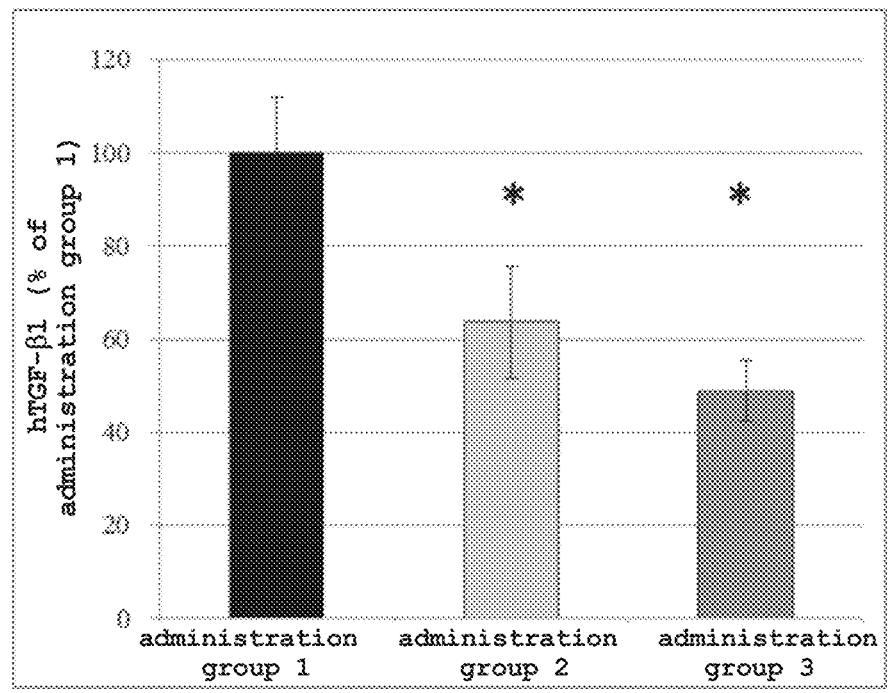
FIG. 15 shows the relative amount of hTGF-β1 in a lung tissue of each administration group of PK-0051.
Figure 16:
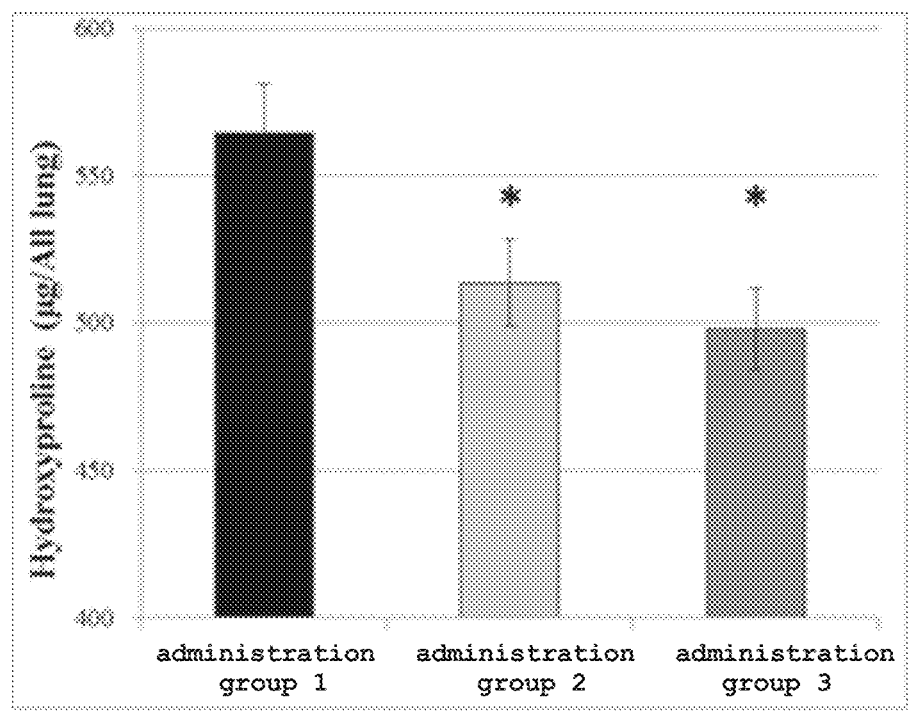
FIG. 16 shows the hydroxy proline amount in a lung tissue of each administration group of PK-0051.

The results are shown in FIG. 15 and FIG. 16. FIG. 15 is a graph showing the TGF-β1 level in each administration group, wherein the vertical axis shows the TGF-β1 level of lung tissue. FIG. 16 is a graph showing the hydroxy proline amount in each administration group, wherein the vertical axis shows the hydroxy proline amount in lung tissue. In TG mouse/nucleic acid molecule solution (0.1 mg/kg) administration group 3, the TGF-β1 level and hydroxy proline amount in the lung tissue were significantly inhibited as compared to TG mouse/0.05 M citrate buffer (pH 6.5) administration group 1.

Therefrom it was shown that PK-0051, which is a nucleic acid molecule in the present invention, inhibits expression of target TGF-β1 also in vivo and inhibits pulmonary fibrosis.

Example 7 (Stability Evaluation of 10, 20, 40 and 80 mg/mL PK-0051-Containing Compositions (pH 6.0))

10, 20, 40 and 80 mg/mL PK-0051-containing compositions (pH 6.0) were prepared, and stability was evaluated.

1. Test Composition

Test composition 174 was prepared as follows. Citric acid hydrate (105.07 g) was dissolved in water for injection (1 L) to give 0.5 M citric acid solution. Similarly, trisodium citrate dihydrate (147.05 g) was dissolved in water for injection (1 L) to give 0.5 M sodium citrate solution. The 0.5 M citric acid solution was added to the 0.5 M sodium citrate solution to adjust the pH to 6.0 to give 0.5 M citrate buffer (pH 6.0). PK-0051 (840 mg) was dissolved in water for injection (8 mL) and used as a stock solution. 4.02 mL of water for injection and 0.5 mL of 0.5 M citrate buffer (pH 6.0) were added to 0.48 mL of the stock solution and the mixture was stirred and passed through a 0.22 μm polyvinylidene difluoride (PVDF) filter.

Test composition 175 was prepared by a method similar to that used for the preparation of test composition 174 except that 3.55 mL of water for injection and 0.5 mL of 0.5 M citrate buffer (pH 6.0) were added to and mixed with 0.95 mL of the stock solution.

Test composition 176 was prepared by a method similar to that used for the preparation of test composition 174 except that 2.6 mL of water for injection and 0.5 mL of 0.5 M citrate buffer (pH 6.0) were added to and mixed with 1.9 mL of the stock solution.

Test composition 177 was prepared by a method similar to that used for the preparation of test composition 174 except that 0.69 mL of water for injection and 0.5 mL of 0.5 M citrate buffer (pH 6.0) were added to and mixed with 3.81 mL of the stock solution.

test composition 174: PK-0051 (0.05 M citrate buffer (pH 6.0)), (10 mg/mL)
test composition 175: PK-0051 (0.05 M citrate buffer (pH 6.0)), (20 mg/mL)
test composition 176: PK-0051 (0.05 M citrate buffer (pH 6.0)), (40 mg/mL)
test composition 177: PK-0051 (0.05 M citrate buffer (pH 6.0)), (80 mg/mL)

2. Evaluation Method

The test compositions 174-177 were respectively placed in four 5 mL glass vials, each containing 1 mL thereof, and stored in a stability test chamber at 60° C. The test compositions were taken out every week and diluted 10-fold. 10 μL of test composition 174, 5 μL of test composition 175, 3 μL of test composition 176 and 2 μL of test composition 177 were measured by HPLC. The measurement was performed until week 4. The content of PK-0051 was calculated, and the stability was evaluated based on a decrease in the content ratio (%) relative to the content at the time of start of the storage. The calculation method of the content and measurement method are shown below.

Using a solution (100%) obtained by dissolving 10-fold the test composition 174 stored separately at 4° C., and solutions obtained by mixing said solution and water for injection at ratios of 9:1, 8:2, 7:3 and 6:4 (90%, 80%, 70% and 60%, respectively) as calibration curve samples, 10 μL each of the calibration curve samples was applied to HPLC to measure peak areas. The regression line (Y=aX+b) (calibration curve) was obtained by the least squares method by plotting the measured values of respective calibration curve samples, with the theoretical content (%) on the horizontal axis (X) and the peak area on the vertical axis (Y). The peak area of the test composition 174 measured by HPLC under the same conditions was applied to the calibration curve to determine a theoretical content (%). The content of test composition 175 was determined by a method similar to the above-mentioned method except that each calibration curve sample (5 μL) produced using test composition 175 was used for HPLC. The content of test composition 176 was determined by a method similar to the above-mentioned method except that each calibration curve sample (3 μL) produced using test composition 176 was used for HPLC. The content of test composition 177 was determined by a method similar to the above-mentioned method except that each calibration curve sample (2 μL) produced using test composition 177 was used for HPLC.

Measurement Method

The calibration curve samples (60%-100%) and respective test compositions were measured under the following measurement conditions.

Ion Exchange HPLC
measurement device: LC-20A SHIMAZU HPLC system (AEX-HPLC), manufactured by Shimadzu Corporation
detector: ultraviolet absorption spectrophotometer (measurement wavelength: 260 nm)
column: DNAPac PA-100 (4×250 mm)
column temperature: 80° C.
mobile phase A: 25 mM Tris-HCL (pH 8.0), 8 M urea, 10% Acetonitrile
mobile phase B: mobile phase A, 700 mM sodium perchlorate monohydrate
feed of mobile phase: The mixing ratio of mobile phase A and mobile phase B was changed as follows to control concentration gradient (Table 4).

TABLE 4

| time (min) after injection | mobile phase A (vol %) | mobile phase B (vol %) |
|---|---|---|
| 0→20 | 90→60 | 10→40 | flow: 1.0 mL/min

3. Results

Figure 17:
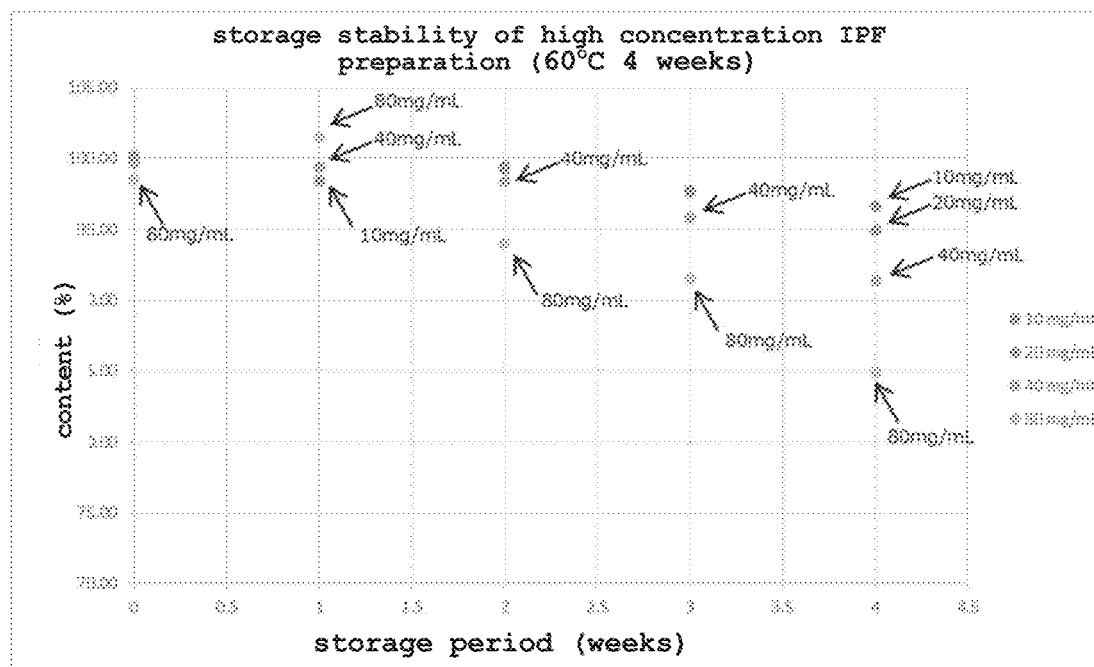
FIG. 17 shows the results of a stability test at 60° C. of 10, 20, 40 and 80 mg/mL PK-0051 (0.05 M citrate buffer (pH 6.0)).
Figure 18:
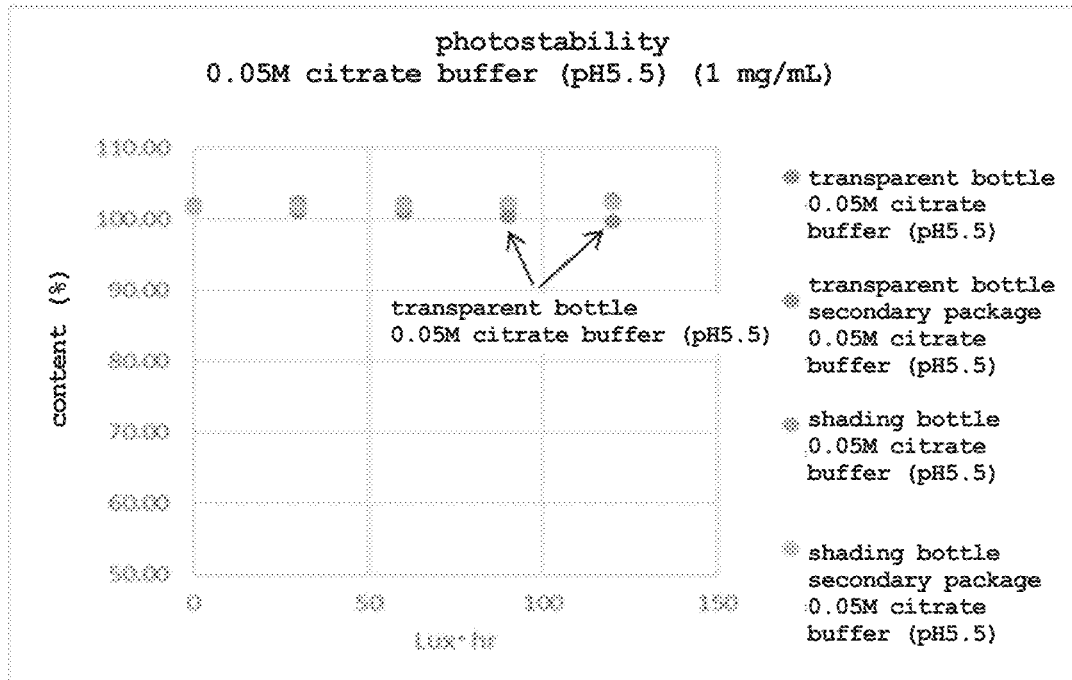
FIG. 18 shows the results of a photostability test of 1 mg/mL PK-0051 (0.05 M citrate buffer (pH 5.5)). Ion exchange HPLC was used for the measurement.
Figure 19:
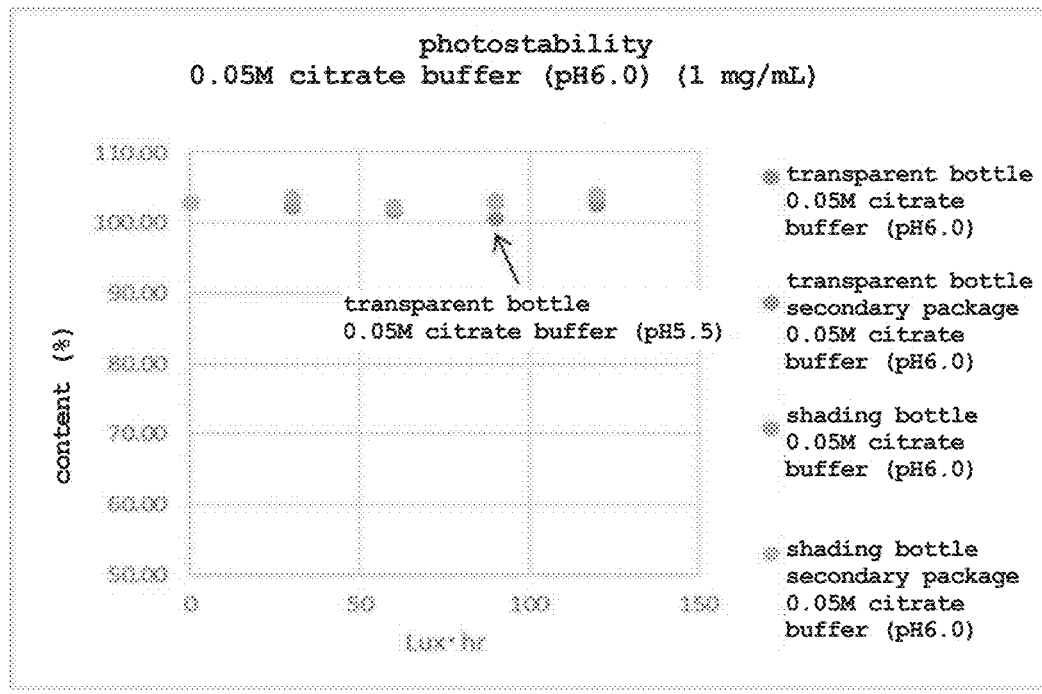
FIG. 19 shows the results of a photostability test of 1 mg/mL PK-0051 (0.05 M citrate buffer (pH 6.0)). Ion exchange HPLC was used for the measurement.
Figure 20:
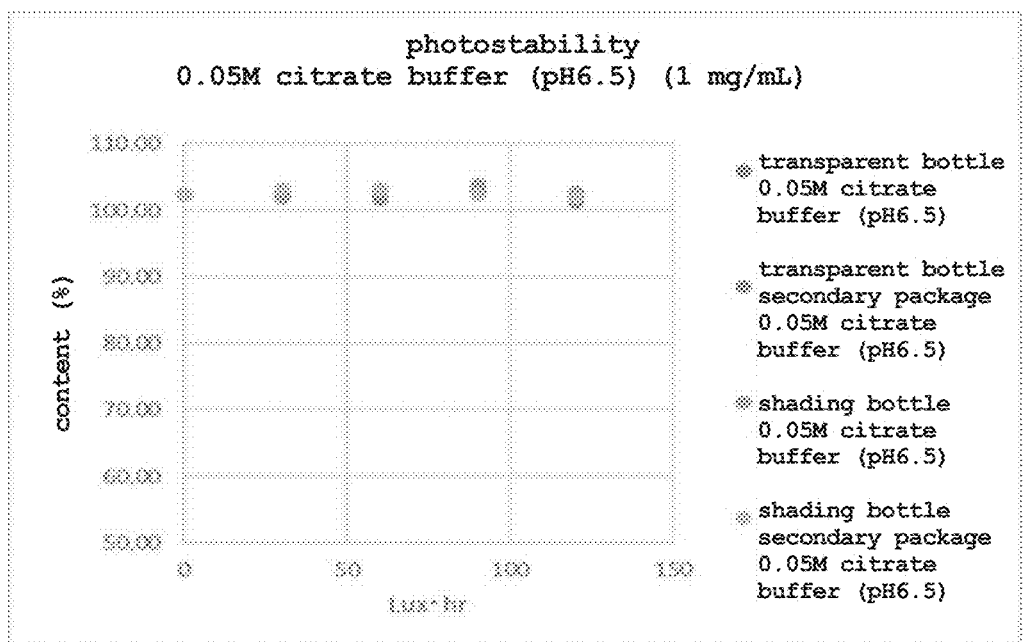
FIG. 20 shows the results of a photostability test of 1 mg/mL PK-0051 (0.05 M citrate buffer (pH 6.5)). Ion exchange HPLC was used for the measurement.
Figure 21:
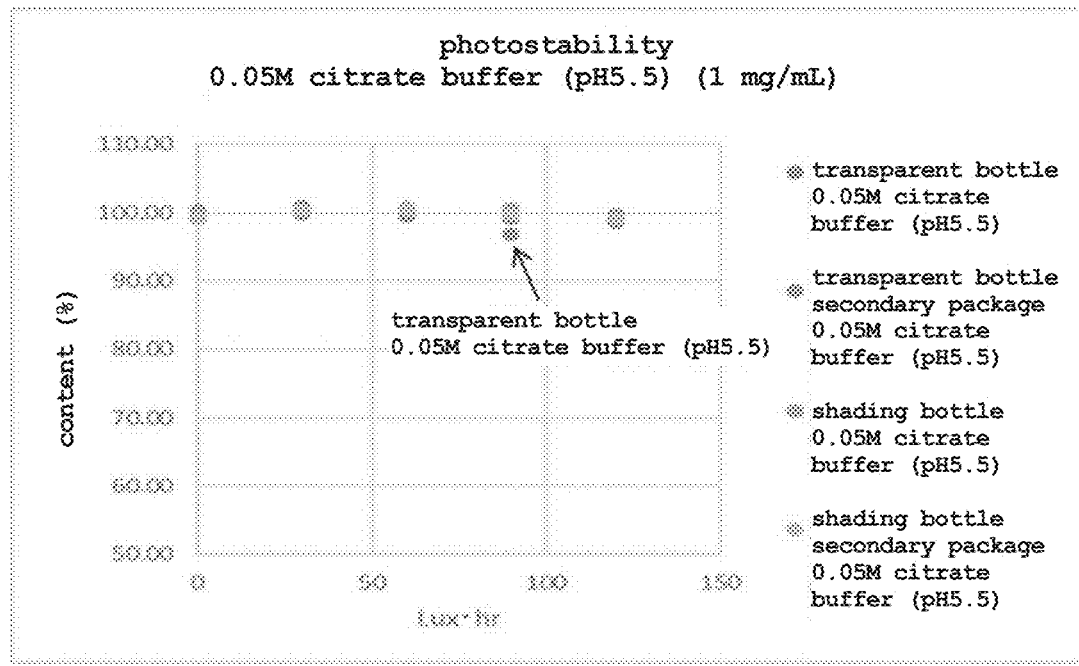
FIG. 21 shows the results of a photostability test of 1 mg/mL PK-0051 (0.05 M citrate buffer (pH 5.5)). Reversed-phase HPLC was used for the measurement.
Figure 22:
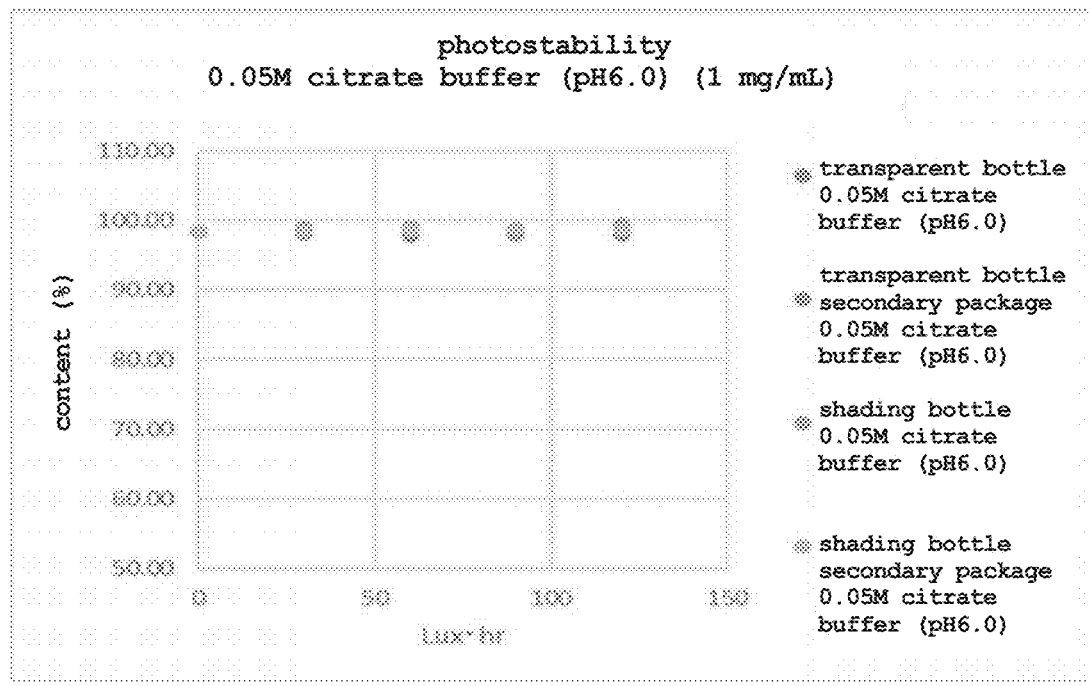
FIG. 22 shows the results of a photostability test of 1 mg/mL PK-0051 (0.05 M citrate buffer (pH 6.0)). Reversed-phase HPLC was used for the measurement.
Figure 23:
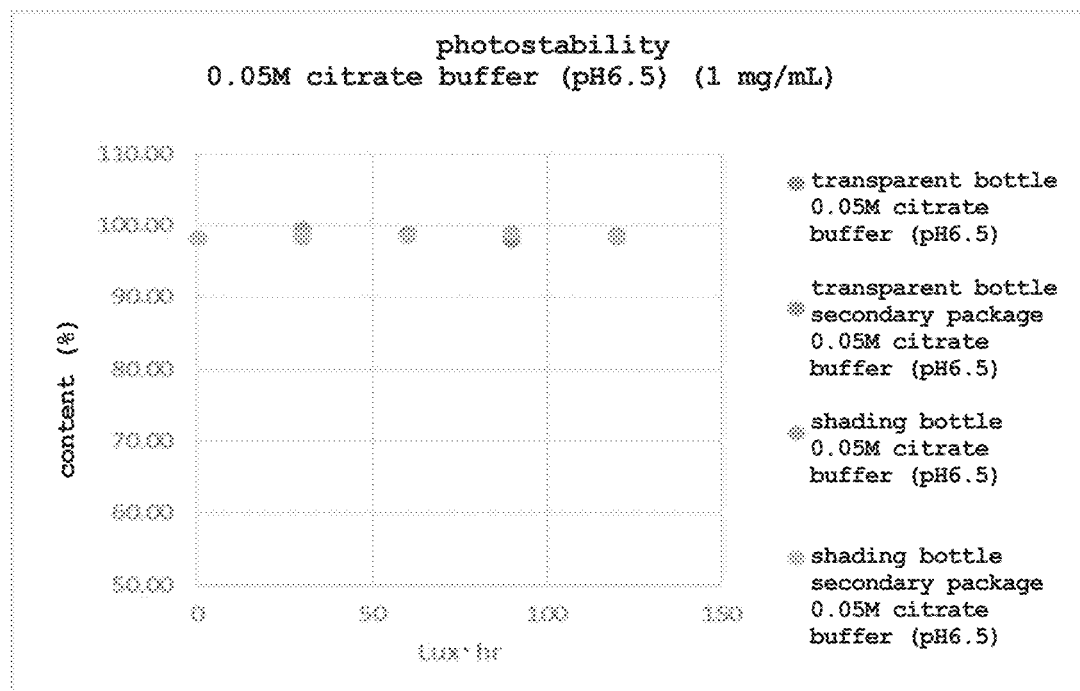
FIG. 23 shows the results of a photostability test of 1 mg/mL PK-0051 (0.05 M citrate buffer (pH 6.5)). Reversed-phase HPLC was used for the measurement.

The results are shown in Table 5 and FIG. 17. After storage at 60° C. for 4 weeks, the content of PK-0051 was about 97% when the concentration of PK-0051 was 10 mg/mL, about 95% when the concentration was 20 mg/mL, about 91% when the concentration was 40 mg/mL, and about 85% when the concentration was 80 mg/mL. It was shown therefrom that the decrease in the content compared with that at the start of the storage increases as the concentration increases. On the contrary, when the concentration of PK-0051 was 10 mg/mL or 20 mg/mL, the decrease in the content compared with that at the time of start of the storage is less than 10%. In addition, even when the concentration of PK-0051 was 80 mg/mL, which was the lowest content, the decrease in the content was about 15%. Therefore, PK-0051 was shown to have high stability even under severe storage conditions of 60° C., 4 weeks.

TABLE 5

| storage period | content (%) of PK-0051 | | | |
|---|---|---|---|---|
| (weeks) | 10 mg/mL | 20 mg/mL | 40 mg/mL | 80 mg/mL |
| 0 | 100.20 | 100.05 | 99.67 | 98.50 |
| 1 | 98.42 | 99.39 | 99.34 | 101.43 |
| 2 | 99.41 | 99.20 | 98.38 | 94.01 |
| 3 | 97.63 | 97.79 | 95.81 | 91.48 |
| 4 | 96.63 | 94.95 | 91.35 | 84.94 |

Example 8 (Stability Evaluation (Photostability) of 1 mg/mL PK-0051-Containing Composition (pH 5.5, 6.0 and 6.5))

Using transparent glass vials and brown glass vials each filled with PK-0051-containing composition, and those further packaged in paper boxes, the stability of PK-0051 to light was evaluated.

1. Test Composition

Test composition 178 was prepared as follows. Citric acid hydrate (21.014 g) was dissolved in water for injection (1 L) to give 0.1 M citric acid solution. Similarly, trisodium citrate dihydrate (29.41 g) was dissolved in water for injection (1 L) to give 0.1 M sodium citrate solution. The 0.1 M citric acid solution was added to the 0.1 M sodium citrate solution to adjust the pH to 5.5 to give 0.1 M citrate buffer (pH 5.5). PK-0051 (210 mg) was dissolved in water for injection (10 mL) and used as a stock solution. 9.5 mL of water for injection and 10.5 mL of 0.1 M citrate buffer (pH 5.5) were added to 1 mL of the stock solution and the mixture was stirred and passed through a 0.22 μm polyvinylidene difluoride (PVDF) filter.

Test composition 179 was prepared by a method similar to that used for the preparation of test composition 178 except that 0.1 M citric acid solution was added to the 0.1 M sodium citrate solution to adjust the pH to 6.0 to give 0.1 M citrate buffer (pH 6.0) and 9.5 mL of water for injection and 10.5 mL of 0.1 M citrate buffer (pH 6.0) were added to and mixed with 1 mL of the stock solution.

Test composition 180 was prepared by a method similar to that used for the preparation of test composition 178 except that 0.1 M citric acid solution was added to the 0.1 M sodium citrate solution to adjust the pH to 6.5 to give 0.1 M citrate buffer (pH 6.5) and 9.5 mL of water for injection and 10.5 mL of 0.1 M citrate buffer (pH 6.5) were added to and mixed with 1 mL of the stock solution.

test composition 178: PK-0051 (0.05 M citrate buffer (pH 5.5)), (1 mg/mL)
test composition 179: PK-0051 (0.05 M citrate buffer (pH 6.0)), (1 mg/mL)
test composition 180: PK-0051 (0.05 M citrate buffer (pH 6.5)), (1 mg/mL)

2. Evaluation Method

The test compositions 178-180 were respectively placed in ten 5 mL transparent glass vials and ten 5 mL brown glass vials (transparent bottles and shading bottles). In addition, transparent bottles and shading bottles similarly filled with test compositions 178-180 were packaged in a paper box (transparent bottle secondary package and shading bottle secondary package). These were stored in a stability test chamber at 25° C./60% RH under a daylight fluorescent lamp (illuminance 1580 Lux), which uses a D65 lamp as a light source, until the total light exposure reached 1.2 million Lux·hr (storage period 32 days, total light exposure 1,213,743 Lux·hr). When the total light exposure reached 0.3 million Lux·hr, 0.6 million Lux·hr, 0.9 million Lux·hr and 1.2 million Lux·hr, the test compositions were taken out and 10 μL thereof was measured by reversed-phase HPLC and ion exchange HPLC. The content of PK-0051 was calculated, and the stability was evaluated based on a decrease in the content ratio (%) relative to the content at the time of start of the storage. The calculation method of the content and measurement method are shown below.

Test composition 178 (100%) prepared similarly to the above (transparent bottles, shading bottles, transparent bottle secondary package and shading bottle secondary package) and stored in a dark place at 4° C. and water for injection were mixed at ratios of 9:1, 8:2, 7:3 and 6:4 and the solutions (90%, 80%, 70% and 60%) were used as calibration curve samples. Each calibration curve sample (10 μL) was applied to reversed-phase HPLC and ion exchange HPLC and the peak area was measured. The regression line (Y=aX+b) (calibration curve) was obtained by the least-squares method by plotting the measured values of each calibration curve sample with the theoretical content (%) on the horizontal axis (X) and the peak area on the vertical axis (Y). The peak area of test composition 178 measured by reversed-phase HPLC and ion exchange HPLC under the same conditions was applied to the calibration curve to determine the theoretical content (%). The contents of test compositions 179 and 180 were determined by a method similar to the above-mentioned method.

Measurement Method

Calibration curve samples (60%-100%) and each test compositions were measured under the following measurement conditions. The measurement by ion exchange HPLC was performed by a measurement method similar to that in Example 7.

Reversed-Phase HPLC measurement device: LC-10A SHIMAZU HPLC system (RP-HPLC), manufactured by Shimadzu Corporation
detector: ultraviolet absorption spectrophotometer (measurement wavelength: 260 nm)
column: X-Bridge OST C18 (2.5 μm, 4.6×50 mm) column
temperature: 40° C.
mobile phase A: 50 mM TEAA (pH 7.0), 0.5% Acetonitrile
mobile phase B: 100% Acetonitrile
feed of mobile phase: The mixing ratio of mobile phase A and mobile phase B was changed as follows to control concentration gradient (Table 6).

TABLE 6

| time (min) after injection | mobile phase A (vol %) | mobile phase B (vol %) |
|---|---|---|
| 0→12 | 100→60 | 0→40 | flow: 1.0 mL/min

3. Results

The results are shown in Tables 7-9 and FIGS. 18-23.

It was clarified that all test compositions showed no definite change in the content by the determination by reversed-phase HPLC or ion exchange HPLC and are stable to light. From the results, it is considered that the composition of the present invention is free of a decrease in the quality of the preparation due to light even when exposed to light in the quantity of 1.2 million Lux·hr during the period of from production to use, and can be handled in the same way as non-exposed products. Furthermore, it is considered that a transparent glass vial, which is lower in cost, can be used instead of a brown glass vial.

TABLE 7 photostability test of PK-0051 in 0.05M citrate buffer (pH 5.5)

| | | content (%) of PK-0051 | |
|---|---|---|---|
| sample name | Lux · hr | ion exchange HPLC | reversed-phase HPLC |
| transparent bottle, dark place at 4° C. | 0 | 101.55 | 99.13 |
| | 30 | 101.10 | 100.95 |
| transparent bottle 0.05M citrate buffer (pH 5.5) | 60 | 100.85 | 99.50 |
| | 90 | 100.28 | 96.83 |
| | 120 | 99.73 | 98.70 |
| transparent bottle secondary package 0.05M citrate buffer (pH 5.5) | 30 | 102.32 | 99.92 |
| | 60 | 102.30 | 100.77 |
| | 90 | 101.86 | 99.13 |
| | 120 | 102.76 | 99.68 |
| shading bottle 0.05M citrate buffer (pH 5.5) | 30 | 101.99 | 100.38 |
| | 60 | 101.79 | 100.26 |
| | 90 | 101.61 | 100.03 |
| | 120 | 102.23 | 100.60 |
| shading bottle secondary package 0.05M citrate buffer (pH 5.5) | 30 | 101.79 | 100.35 |
| | 60 | 101.87 | 100.52 |
| | 90 | 102.43 | 99.70 |
| | 120 | 102.20 | 99.12 |

TABLE 8 photostability test of PK-0051 in 0.05M citrate buffer (pH 6.0)

| | | content (%) of PK-0051 | |
|---|---|---|---|
| sample name | Lux · hr | ion exchange HPLC | reversed-phase HPLC |
| transparent bottle, dark place at 4° C. | 0 | 102.83 | 98.35 |
| transparent bottle 0.05M citrate buffer (pH 6.0) | 30 | 102.24 | 98.83 |
| | 60 | 101.65 | 97.75 |
| | 90 | 100.57 | 98.09 |
| | 120 | 102.62 | 97.93 |
| transparent bottle secondary package 0.05M citrate buffer (pH 6.0) | 30 | 102.41 | 98.21 |
| | 60 | 102.35 | 99.07 |
| | 90 | 103.23 | 98.07 |
| | 120 | 103.00 | 99.18 |
| shading bottle 0.05M citrate buffer (pH 6.0) | 30 | 102.46 | 98.44 |
| | 60 | 102.17 | 98.60 |
| | 90 | 102.94 | 97.98 |
| | 120 | 104.15 | 99.33 |
| shading bottle secondary package 0.05M citrate buffer (pH 6.0) | 30 | 103.70 | 98.52 |
| | 60 | 102.12 | 98.68 |
| | 90 | 103.16 | 98.83 |
| | 120 | 104.11 | 98.65 |

TABLE 9 photostability test of PK-0051 in 0.05M citrate buffer (pH 6.5)

| | | content (%) of PK-0051 | |
|---|---|---|---|
| sample name | Lux · hr | ion exchange HPLC | reversed-phase HPLC |
| transparent bottle, dark place at 4° C. | 0 | 102.41 | 98.20 |
| transparent bottle 0.05M citrate buffer (pH 6.5) | 30 | 102.57 | 98.53 |
| | 60 | 102.12 | 98.77 |
| | 90 | 103.14 | 97.82 |
| | 120 | 101.23 | 98.71 |
| transparent bottle secondary package 0.05M citrate buffer (pH 6.5) | 30 | 102.15 | 98.26 |
| | 60 | 101.71 | 98.92 |
| | 90 | 102.85 | 98.00 |
| | 120 | 102.54 | 98.20 |
| shading bottle 0.05M citrate buffer (pH 6.5) | 30 | 101.83 | 99.63 |
| | 60 | 103.21 | 98.62 |
| | 90 | 103.97 | 99.12 |
| | 120 | 102.73 | 98.74 |
| shading bottle secondary package 0.05M citrate buffer (pH 6.5) | 30 | 103.23 | 98.33 |
| | 60 | 103.04 | 98.36 |
| | 90 | 102.43 | 98.85 |
| | 120 | 101.85 | 98.37 |

Example 9 (Stability Evaluation of PK-0051-Containing Composition with Osmotic Pressure Ratio Adjusted by Isotonicity Agent)

Using various isotonicity agents (NaCl, KCl, glycerol, D-mannitol, lactitol, D-sorbitol, and sucrose), the ratio of osmotic pressure of PK-0051-containing composition was adjusted to 1±0.1 and the stability was evaluated.

1. Test Composition

Test composition 181 was prepared as follows. Citric acid hydrate (105.07 g) was dissolved in water for injection (1 L) to give 0.5 M citric acid solution. Similarly, trisodium citrate dihydrate (147.05 g) was dissolved in water for injection (1 L) to give 0.5 M sodium citrate solution. The 0.5 M citric acid solution was added to the 0.5 M sodium citrate solution to adjust the pH to 6.0 to give 0.5 M citrate buffer (pH 6.0). 1 g of NaCl was dissolved in 10 mL of water for injection to give a 10% solution. PK-0051 (210 mg) was dissolved in water for injection (140 mL) and used as a stock solution. 0.68 mL of NaCl 10% solution, 11.82 mL of water for injection and 1.5 mL of 0.5 M citrate buffer (pH 6.0) were added to 1 mL of the stock solution and the mixture was stirred and passed through a 0.22 μm polyvinylidene difluoride (PVDF) filter.

Test composition 182 was prepared by a method similar to that used for the preparation of test composition 181 except that KCl was used instead of NaCl, and 0.85 mL of KCl 10% solution, 11.65 mL of water for injection and 1.5 mL of 0.5 M citrate buffer (pH 6.0) were added to and mixed with 1 mL of the stock solution.

Test composition 183 was prepared by a method similar to that used for the preparation of test composition 181 except that glycerol was used instead of NaCl, and 1.8 mL of glycerol 10% solution, 10.7 mL of water for injection and 1.5 mL of 0.5 M citrate buffer (pH 6.0) were added to and mixed with 1 mL of the stock solution.

Test composition 184 was prepared by a method similar to that used for the preparation of test composition 181 except that D-mannitol was used instead of NaCl, and 3.75 mL of D-mannitol 10% solution, 8.75 mL of water for injection and 1.5 mL of 0.5 M citrate buffer (pH 6.0) were added to and mixed with 1 mL of the stock solution.

Test composition 185 was prepared by a method similar to that used for the preparation of test composition 181 except that lactitol was used instead of NaCl, and 7.05 mL of lactitol 10% solution, 5.45 mL of water for injection and 1.5 mL of 0.5 M citrate buffer (pH 6.0) were added to and mixed with 1 mL of the stock solution.

Test composition 186 was prepared by a method similar to that used for the preparation of test composition 181 except that D-sorbitol was used instead of NaCl, and 3.75 mL of D-sorbitol 10% solution, 8.75 mL of water for injection and 1.5 mL of 0.5 M citrate buffer (pH 6.0) were added to and mixed with 1 mL of the stock solution.

Test composition 187 was prepared by a method similar to that used for the preparation of test composition 181 except that sucrose was used instead of NaCl, and 7 mL of sucrose 10% solution, 5.5 mL of water for injection and 1.5 mL of 0.5 M citrate buffer (pH 6.0) were added to and mixed with 1 mL of the stock solution.

Test composition 188 was prepared by a method similar to that used for the preparation of test composition 181 except that 12.5 mL of water for injection and 1.5 mL of 0.5 M citrate buffer (pH 6.0) were added to and mixed with 1 mL of the stock solution.

Test composition 189 was prepared by a method similar to that used for the preparation of test composition 181 except that 12.65 mL of water for injection and 1.35 mL of NaCl 10% solution were added to and mixed with 1 mL of the stock solution.

test composition 181: PK-0051 (0.05 M citrate buffer (pH 6.0)/NaCl (osmotic pressure ratio of 1)), (0.1 mg/mL)
test composition 182: PK-0051 (0.05 M citrate buffer (pH 6.0)/KCl (osmotic pressure ratio of 1)), (0.1 mg/mL)
test composition 183: PK-0051 (0.05 M citrate buffer (pH 6.0)/glycerol (osmotic pressure ratio of 1)), (0.1 mg/mL)
test composition 184: PK-0051 (0.05 M citrate buffer (pH 6.0)/D-mannitol (osmotic pressure ratio of 1)), (0.1 mg/mL)
test composition 185: PK-0051 (0.05 M citrate buffer (pH 6.0)/lactitol (osmotic pressure ratio of 1)), (0.1 mg/mL)
test composition 186: PK-0051 (0.05 M citrate buffer (pH 6.0)/D-sorbitol (osmotic pressure ratio of 1)), (0.1 mg/mL)
test composition 187: PK-0051 (0.05 M citrate buffer (pH 6.0)/sucrose (osmotic pressure ratio of 1)), (0.1 mg/mL)
test composition 188: PK-0051 (0.05 M citrate buffer (pH 6.0)), (0.1 mg/mL)

test composition 189: PK-0051 (NaCl (osmotic pressure ratio of 1)), (0.1 mg/mL)

2. Evaluation Method

The test compositions 181-189 were respectively placed in fourteen 5 mL glass vials, each containing 1 mL thereof, and stored in stability test chambers at 25° C./60% RH, 40° C./75% RH and 60° C. One and two weeks later, each test composition (30 μL) was measured by reversed-phase HPLC and ion exchange HPLC.

Test compositions 181-189 were subjected to an acceleration test under conditions (105° C. and 121° C. for 5 min and 15 min) corresponding to the storage at 60° C. for 4 weeks.

Test compositions 181-189 were respectively subjected to an autoclave treatment under four conditions of 105° C. for 5 min, 105° C. for 15 min, 121° C. for 5 min, and 121° C. for 15 min, and 30 μL was measured by reversed-phase HPLC and ion exchange HPLC.

After measurement by HPLC, the content of PK-0051 was calculated, and the stability was evaluated based on a decrease in the content ratio (%) relative to the content at the time of start of the storage. The calculation method of the content and measurement method are shown below.

Solutions (90%, 80%, 70% and 60%) obtained by mixing test composition 188 (100%) and water for injection at 9:1, 8:2, 7:3 and 6:4, respectively were used as calibration curve samples, 30 μL each of the calibration curve samples was applied to HPLC to measure peak areas, the measured values of respective calibration curve samples were plotted with the theoretical content (%) on the horizontal axis (X) and the peak area on the vertical axis (Y), a regression line (Y=aX+b) (calibration curve) was obtained by the least squares method and applying the peak area of the test composition measured by HPLC under the same conditions to the calibration curve, whereby theoretical content (%) was obtained.

Measurement Method

The calibration curve samples (60%-100%) and test compositions were measured under the following measurement conditions. The measurement by ion exchange HPLC was performed by a measurement method similar to that in Example 7. The measurement by reversed-phase HPLC was performed by a measurement method similar to that in Example 8 except that 50 mM TEAA (pH 7.3) was used as mobile phase A and the measurement wavelength was 254 nm.

3. Results

The results are shown in Tables 10-18. Test compositions 181-188 showed no definite decrease in the content of PK-0051 after storage at 25° C., 40° C. or 60° C. for 2 weeks. Test compositions 181-188 showed a decrease within about 15% in the content of PK-0051 by an autoclave treatment (105° C. and 121° C. for 5 min and 15 min), thus exhibiting high stability. On the other hand, test composition 189 showed no definite decrease in the content of PK-0051 after storage at 25° C., 40° C. or 60° C. for 2 weeks; however, a decrease in the content of PK-0051 due to an autoclave treatment (121° C. for 5 min and 15 min) was remarkably found (about 24% decrease by 121° C. for 5 min, about 41% decrease by 121° C. for 15 min). It was also clarified that the stability decreases due to an influence of NaCl in the absence of 0.05 M citrate buffer (pH 6.0). The above results have clarified that an isotonicity agent does not decrease stability of PK-0051 in 0.05 M citrate buffer (pH 6.0).

TABLE 10 thermal stability of PK-0051 in 0.05M citrate buffer (pH 6.0)/NaCl (osmotic pressure ratio of 1)

| sample name | storage temperature or autoclave treatment temperature | storage period | content (%) of PK-0051 | |
|---|---|---|---|---|
| | | | reversed-phase HPLC | ion exchange HPLC |
| test composition 181 PK-0051 (0.05M citrate buffer (pH 6.0)/NaCl (osmotic pressure ratio of 1)), (0.1 mg/mL) | 25° C. | at time of start | 101.70 | 103.70 |
| | | 1 week | 102.08 | 101.15 |
| | | 2 weeks | 102.73 | 101.45 |
| | 40° C. | at time of start | 101.70 | 103.70 |
| | | 1 week | 102.37 | 101.19 |
| | | 2 weeks | 101.32 | 101.02 |
| | 60° C. | at time of start | 101.70 | 103.70 |
| | | 1 week | 102.36 | 100.99 |
| | | 2 weeks | 101.39 | 98.83 |
| | autoclave 105° C. | at time of start | 101.70 | 103.70 |
| | | 5 min | 99.43 | 101.67 |
| | | 15 min | 98.06 | 97.32 |
| | autoclave 121° C. | at time of start | 101.70 | 103.70 |
| | | 5 min | 95.16 | 96.58 |
| | | 15 min | 90.00 | 86.90 |

TABLE 11 thermal stability of PK-0051 in 0.05M citrate buffer (pH 6.0)/KCl (osmotic pressure ratio of 1)

| sample name | storage temperature or autoclave treatment temperature | storage period | content (%) of PK-0051 | |
|---|---|---|---|---|
| | | | reversed-phase HPLC | ion exchange HPLC |
| test composition 182 PK-0051 (0.05M citrate buffer (pH 6.0)/KCl (osmotic pressure ratio of 1)), (0.1 mg/mL) | 25° C. | at time of start | 101.05 | 102.22 |
| | | 1 week | 101.41 | 98.79 |
| | | 2 weeks | 102.24 | 100.44 |
| | 40° C. | at time of start | 101.05 | 102.22 |
| | | 1 week | 101.70 | 100.47 |
| | | 2 weeks | 102.07 | 99.52 |
| | 60° C. | at time of start | 101.05 | 102.22 |
| | | 1 week | 101.46 | 100.02 |
| | | 2 weeks | 100.94 | 98.44 |
| | autoclave 105° C. | at time of start | 101.05 | 102.22 |
| | | 5 min | 99.65 | 99.94 |
| | | 15 min | 97.27 | 96.70 |
| | autoclave 121° C. | at time of start | 101.05 | 102.22 |
| | | 5 min | 95.44 | 95.16 |
| | | 15 min | 88.63 | 85.79 |

TABLE 12 thermal stability of PK-0051 in 0.05M citrate buffer (pH 6.0)/glycerol (osmotic pressure ratio of 1)

| sample name | storage temperature or autoclave treatment temperature | storage period | content (%) of PK-0051 reversed-phase HPLC | ion exchange HPLC |
|---|---|---|---|---|
| test composition 183 PK-0051 (0.05M citrate buffer (pH 6.0)/glycerol (osmotic pressure ratio of 1)), (0.1 mg/mL) | 25° C. | at time of start | 101.27 | 102.24 |
| | | 1 week | 101.73 | 101.23 |
| | | 2 weeks | 102.55 | 97.82 |
| | 40° C. | at time of start | 101.27 | 102.24 |
| | | 1 week | 101.52 | 101.35 |
| | | 2 weeks | 102.98 | 102.18 |
| | 60° C. | at time of start | 101.27 | 102.24 |
| | | 1 week | 102.09 | 99.25 |
| | | 2 weeks | 100.87 | 99.72 |
| | autoclave 105° C. | at time of start | 101.27 | 102.24 |
| | | 5 min | 100.22 | 100.87 |
| | | 15 min | 98.78 | 97.78 |
| | autoclave 121° C. | at time of start | 101.27 | 102.24 |
| | | 5 min | 95.17 | 95.77 |
| | | 15 min | 91.04 | 86.41 |

TABLE 13 thermal stability of PK-0051 in 0.05M citrate buffer (pH 6.0)/D-mannitol (osmotic pressure ratio of 1)

| sample name | storage temperature or autoclave treatment temperature | storage period | content (%) of PK-0051 reversed-phase HPLC | ion exchange HPLC |
|---|---|---|---|---|
| test composition 184 PK-0051 (0.05M citrate buffer (pH 6.0)/D-mannitol (osmotic pressure ratio of D), (0.1 mg/mL) | 25° C. | at time of start | 101.86 | 102.32 |
| | | 1 week | 102.42 | 101.18 |
| | | 2 weeks | 102.59 | 98.52 |
| | 40° C. | at time of start | 101.86 | 102.32 |
| | | 1 week | 102.40 | 101.57 |
| | | 2 weeks | 102.85 | 100.76 |
| | 60° C. | at time of start | 101.86 | 102.32 |
| | | 1 week | 102.00 | 101.13 |
| | | 2 weeks | 101.20 | 100.12 |
| | autoclave 105° C. | at time of start | 101.86 | 102.32 |
| | | 5 min | 100.35 | 100.79 |
| | | 15 min | 98.86 | 97.25 |
| | autoclave 121° C. | at time of start | 101.86 | 102.32 |
| | | 5 min | 95.58 | 95.85 |
| | | 15 min | 90.14 | 86.95 |

TABLE 14 thermal stability of PK-0051 in 0.05M citrate buffer (pH 6.0)/lactitol (osmotic pressure ratio of 1)

| sample name | storage temperature or autoclave treatment temperature | storage period | content (%) of PK-0051 reversed-phase HPLC | ion exchange HPLC |
|---|---|---|---|---|
| test composition 185 PK-0051 (0.05M citrate buffer (pH 6.0)/lactitol (osmotic pressure ratio of 1)), (0.1 mg/mL) | 25° C. | at time of start | 102.18 | 102.70 |
| | | 1 week | 102.37 | 101.06 |
| | | 2 weeks | 101.12 | 102.50 |
| | 40° C. | at time of start | 102.18 | 102.70 |
| | | 1 week | 103.15 | 101.60 |
| | | 2 weeks | 101.84 | 101.04 |
| | 60° C. | at time of start | 102.18 | 102.70 |
| | | 1 week | 102.63 | 101.45 |
| | | 2 weeks | 101.62 | 100.04 |
| | autoclave 105° C. | at time of start | 102.18 | 102.70 |
| | | 5 min | 100.15 | 100.79 |
| | | 15 min | 99.01 | 98.17 |
| | autoclave 121° C. | at time of start | 102.18 | 102.70 |
| | | 5 min | 95.54 | 96.00 |
| | | 15 min | 90.80 | 87.74 |

TABLE 15 thermal stability of PK-0051 in 0.05M citrate buffer (pH 6.0)/D-sorbitol (osmotic pressure ratio of 1)

| sample name | storage temperature or autoclave treatment temperature | storage period | content (%) of PK-0051 reversed-phase HPLC | ion exchange HPLC |
|---|---|---|---|---|
| test composition 186 PK-0051 (0.05M citrate buffer (pH 6.0)/D-sorbitol (osmotic pressure ratio of 1)), (0.1 mg/mL) | 25° C. | at time of start | 101.42 | 102.53 |
| | | 1 week | 101.93 | 100.91 |
| | | 2 weeks | 102.21 | 99.73 |
| | 40° C. | at time of start | 101.42 | 102.53 |
| | | 1 week | 102.16 | 101.24 |
| | | 2 weeks | 101.99 | 102.88 |
| | 60° C. | at time of start | 101.42 | 102.53 |
| | | 1 week | 102.01 | 100.98 |
| | | 2 weeks | 100.04 | 99.18 |
| | autoclave 105° C. | at time of start | 101.42 | 102.53 |
| | | 5 min | 99.66 | 100.91 |
| | | 15 min | 98.05 | 96.94 |
| | autoclave 121° C. | at time of start | 101.42 | 102.53 |
| | | 5 min | 95.35 | 94.84 |
| | | 15 min | 90.10 | 85.32 |

TABLE 16 thermal stability of PK-0051 in 0.05M citrate buffer (pH 6.0)/sucrose (osmotic pressure ratio of 1)

| sample name | storage temperature or autoclave treatment temperature | storage period | content (%) of PK-0051 reversed-phase HPLC | ion exchange HPLC |
|---|---|---|---|---|
| test composition 187 PK-0051 (0.05M citrate buffer (pH 6.0)/sucrose (osmotic pressure ratio of 1)), (0.1 mg/mL) | 25° C. | at time of start | 102.10 | 103.37 |
| | | 1 week | 102.49 | 101.67 |
| | | 2 weeks | 101.15 | 102.00 |
| | 40° C. | at time of start | 102.10 | 103.37 |
| | | 1 week | 102.60 | 99.59 |
| | | 2 weeks | 102.90 | 101.39 |
| | 60° C. | at time of start | 102.10 | 103.37 |
| | | 1 week | 102.56 | 103.63 |
| | | 2 weeks | 101.52 | 101.59 |
| | autoclave 105° C. | at time of start | 102.10 | 103.37 |
| | | 5 min | 100.44 | 101.87 |
| | | 15 min | 99.24 | 96.84 |
| | autoclave 121° C. | at time of start | 102.10 | 103.37 |
| | | 5 min | 95.52 | 95.98 |
| | | 15 min | 90.15 | 87.35 |

TABLE 17 thermal stability of PK-0051 in 0.05M citrate buffer (pH 6.0)

| sample name | storage temperature or autoclave treatment temperature | storage period | content (%) of PK-0051 reversed-phase HPLC | ion exchange HPLC |
|---|---|---|---|---|
| test composition 188 PK-0051 (0.05M citrate buffer (pH 6.0)), (0.1 mg/mL) | 25° C. | at time of start | 101.72 | 100.97 |
| | | 1 week | 102.32 | 101.09 |
| | | 2 weeks | 102.98 | 103.16 |
| | 40° C. | at time of start | 101.72 | 103.27 |
| | | 1 week | 102.37 | 101.54 |
| | | 2 weeks | 102.67 | 101.55 |
| | 60° C. | at time of start | 101.72 | 103.27 |
| | | 1 week | 102.45 | 103.33 |
| | | 2 weeks | 102.07 | 101.72 |
| | autoclave 105° C. | at time of start | 101.72 | 103.27 |
| | | 5 min | 100.51 | 100.92 |
| | | 15 min | 99.04 | 97.67 |
| | autoclave 121° C. | at time of start | 101.72 | 103.27 |
| | | 5 min | 95.83 | 98.21 |
| | | 15 min | 89.65 | 87.45 |

TABLE 18 thermal stability of PK-0051 in NaCl (osmotic pressure ratio of 1)

| sample name | storage temperature or autoclave treatment temperature | storage period | content (%) of PK-0051 reversed-phase HPLC | ion exchange HPLC |
|---|---|---|---|---|
| test composition 189 PK-0051(NaCl (osmotic pressure ratio of 1)), (0.1 mg/mL) | 25° C. | at time of start | 101.19 | 102.38 |
| | | 1 week | 101.13 | 100.86 |
| | | 2 weeks | 101.98 | 101.07 |
| | 40° C. | at time of start | 101.19 | 102.38 |
| | | 1 week | 101.71 | 101.30 |
| | | 2 weeks | 101.89 | 100.17 |
| | 60° C. | at time of start | 101.19 | 102.38 |
| | | 1 week | 99.57 | 100.41 |
| | | 2 weeks | 95.09 | 91.67 |
| | autoclave 105° C. | at time of start | 101.19 | 102.38 |
| | | 5 min | 95.59 | 96.12 |
| | | 15 min | 93.82 | 94.94 |
| | autoclave 121° C. | at time of start | 101.19 | 102.38 |
| | | 5 min | 78.25 | 75.92 |
| | | 15 min | 62.71 | 58.85 |

INDUSTRIAL APPLICABILITY

According to the present invention, the single-stranded nucleic acid molecule PK-0051 capable of inhibiting expression of TGF-β1 can be stably stored in a solution state at ambient temperature for a long term. Therefore, the present invention is extremely useful in that it can provide a nucleic acid pharmaceutical product that can be stored and transported conveniently, does not require preparation by redissolving when in use, and is superior in handling.

This application is based on a patent application No. 2015-215207 filed in Japan (filing date: Oct. 30, 2015), the contents of which are incorporated in full herein.

The invention claimed is:

1. A composition comprising a single-stranded nucleic acid molecule consisting of a nucleotide sequence shown by

5'-AGCAGAGUACACACAGCAUAUACC (SEQ ID NO: 1)

-P-GGUAUAUGCUGUGUGUACUCUGCUUC-P-G-3' (SEQ ID NO: 2)

-P-G-3', wherein P is a proline derivative linker represented by formula (I)

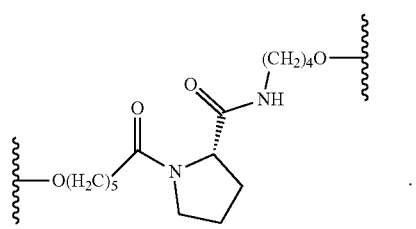

and a buffer, and having the following features:
  (a) being in the form of a solution at ambient temperature;
  (b) the pH of the composition is not less than 4.6 and not more than 7.0; and
  (c) the concentration of the nucleic acid molecule is not more than 80 mg/mL.

2. The composition according to claim 1, wherein the pH of the composition is not less than 5.5 and not more than 6.5.

3. The composition according to claim 1, wherein the buffer comprises one or more buffering agents selected from sodium hydrogen phosphate, sodium dihydrogen phosphate, disodium hydrogen phosphate, sodium chloride, arginine hydrochloride, sodium citrate, trisodium citrate dihydrate, monosodium L-glutamate, sodium acetate, sodium carbonate, sodium hydrogen carbonate, sodium lactate, monopotassium phosphate, sodium hydroxide, meglumine, glycine, citric acid, and acetic acid.

4. The composition according to claim 1, wherein the buffer comprises citric acid and/or phosphoric acid.

5. The composition according to claim 1, further comprising an isotonicity agent.

6. The composition according to claim 5, wherein the isotonicity agent is one or more selected from D-sorbitol, sodium chloride, glycerol, D-mannitol, potassium chloride, lactitol and sucrose.

7. The composition according to claim 1, which is a pharmaceutical composition.

8. A method of producing the composition according to claim 1, comprising dissolving the aforementioned nucleic acid molecule in a buffer to adjust a pH of the composition to not less than 4.6 and not more than 7.0, and storing the solution at ambient temperature.

9. The method according to claim 8, wherein the buffer comprises citric acid and/or phosphoric acid.

10. The method according to claim 8, wherein the composition is a pharmaceutical composition.

11. A method for storing a nucleic acid molecule in a composition so that a content of the nucleic acid molecule after storage at 25° C. and relative humidity of 60% for 4 weeks, is not less than 80% relative to the content at the time of start of the storage, comprising dissolving the nucleic acid molecule in a buffer to adjust a pH of the composition to not less than 5.5 and not more than 6.5, and storing the solution at ambient temperature, wherein the nucleic acid molecule consists of a nucleotide sequence shown by

5'-AGCAGAGUACACACAGCAUAUACC (SEQ ID NO: 1)

-P-GGUAUAUGCUGUGUGUACUCUGCUUC-P-G-3' (SEQ ID NO: 2)

P-G-3', wherein P is a proline derivative linker represented by formula (I)

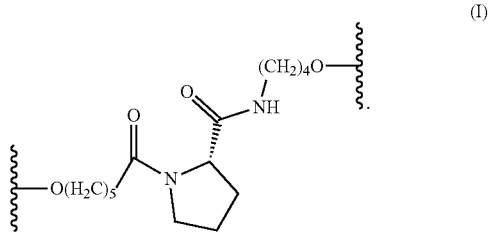

12. The method according to claim 11, wherein the buffer comprises citric acid and/or phosphoric acid.

13. The method according to claim 11, wherein the solution is a pharmaceutical composition.

14. The method according to claim 8, wherein the pH of the composition is not less than 5.5 and not more than 6.5.

* * * * *

SEQUENCE LISTING

<160> NUMBER OF SEQ ID NOS: 2

<210> SEQ ID NO 1
<211> LENGTH: 24
<212> TYPE: RNA
<213> ORGANISM: Artificial Sequence
<220> FEATURE:
<223> OTHER INFORMATION: Synthetic nucleic acid molecule

<400> SEQUENCE: 1

```
agcagaguac acacagcaua uacc                                        24

<210> SEQ ID NO 2
<211> LENGTH: 26
<212> TYPE: RNA
<213> ORGANISM: Artificial Sequence
<220> FEATURE:
<223> OTHER INFORMATION: Synthetic nucleic acid molecule

<400> SEQUENCE: 2
gguauaugcu guguguacuc ugcuuc                                      26
```